(12) United States Patent
Perlingeiro et al.

(10) Patent No.: US 9,850,497 B2
(45) Date of Patent: Dec. 26, 2017

(54) GENE TARGETING METHODS AND TOOLS

(71) Applicant: Regents of the University of Minnesota, Minneapolis, MN (US)

(72) Inventors: Rita Perlingeiro, Minneapolis, MN (US); Michael Kyba, St. Paul, MN (US); Fabrizio Rinaldi, Minneapolis, MN (US); Daniel F. Voytas, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 139 days.

(21) Appl. No.: 14/532,684

(22) Filed: Nov. 4, 2014

(65) Prior Publication Data
US 2015/0125429 A1 May 7, 2015

Related U.S. Application Data

(60) Provisional application No. 61/899,747, filed on Nov. 4, 2013.

(51) Int. Cl.
*C12N 5/00* (2006.01)
*C12N 15/85* (2006.01)
*C12N 15/87* (2006.01)
*C12N 15/11* (2006.01)
*A61K 35/545* (2015.01)
*A61K 48/00* (2006.01)
*C12N 15/10* (2006.01)

(52) U.S. Cl.
CPC ............ *C12N 15/85* (2013.01); *C12N 15/111* (2013.01); *C12N 15/87* (2013.01); *A61K 35/545* (2013.01); *A61K 48/005* (2013.01); *C12N 15/102* (2013.01); *C12N 2310/11* (2013.01); *C12N 2320/34* (2013.01)

(58) Field of Classification Search
CPC ................................ C12N 15/85; C12N 15/87
See application file for complete search history.

(56) References Cited

U.S. PATENT DOCUMENTS 9,393,257 B2 * 7/2016 Osborn .............. A61K 31/7088

OTHER PUBLICATIONS

Maeder and Gersbach. Official Journal of the American Society of Gene & Cell Therapy 24(3):430-446, 2016.*
Kildeback and Porteus, Molecular Therapy, 20(Supplement 1):S89, Abstract No. 227, May 2012.*
Li et al. Stem Cell Reports 4:143-154, 2015.*
Gaj. Trends in Biotechnology 31(7):397-405, 2013.*
Koenig, M., et al., "Complete cloning of the duchenne muscular dystrophy (DMD) cDNA and preliminary genomic organization of the DMD gene in normal and affected individuals", Cell, 50(3), (1987), 509-517.
Roberts, Roland G., et al., "Dystrophins and dystrobrevins", Genome Biology, 2(4), (2001), 1-7.

* cited by examiner

*Primary Examiner* — Marcia S Noble
(74) *Attorney, Agent, or Firm* — Schwegman Lundberg & Woessner, P.A.

(57) ABSTRACT

Provided herein is a general method of correcting a gene, for example a gene with many known mutations, such as a gene with mutations in many different exons which could vary from subject to subject (e.g., patient), as well as a set of tools (TALENs and gene targeting vectors) to accomplish such method.

6 Claims, 3 Drawing Sheets

A.

GENE TARGETING METHODS AND TOOLS

RELATED APPLICATION

This application claims priority from U.S. Provisional Application Ser. No 61/899,747 filed Nov. 4, 2013.

BACKGROUND

Current gene therapy tools (e.g., viral-mediated gene-addition) rely on the provision of functional copies of a therapeutic gene that integrate at random or semi-random into the genome. The consequences of the random integration are perturbation of the locus where the cargo lands and potential gene inactivation or dysregulation (off target effects). These can result in life threatening side effects to the patient.

Duchenne muscular dystrophy (DMD) is a common, genetic neuromuscular disease associated with the progressive deterioration of muscle function, first described over 150 years ago by the French neurologist, Duchenne de Boulogne, after whom the disease is named. DMD has been characterized as an X-linked recessive disorder that affects 1 in 5,000 males caused by mutations in the dystrophin gene. The gene is the largest in the human genome, encompassing 2.6 million base pairs of DNA and containing 79 exons, with mutations scattered across most exons. The dystrophin gene is located in the subregion 21 of the short arm of the X-chromosome. (Roberts, R G., et al., Genomics, 16:536-538(1993)). The transcript of the dystrophin gene is spliced into the mature 14 kb mRNA. The dystrophin gene is located in the subregion 21 of the short arm of the X-chromosome. The transcript of the dystrophin gene is spliced into a mature 14 kb mRNA.

Approximately 60% of dystrophin mutations are large insertion or deletions that lead to frameshift errors downstream, whereas approximately 40% are point mutations or small frameshift rearrangements. The vast majority of DMD patients lack the dystrophin protein. No drug is so far available for effective treatment of DMD, and therefore development of a drug for its treatment has been longed for by patients across the world. In 1987, dystrophin gene, the causative gene of DMD, was found by means of retrospective genetics, and Becker Muscular Dystrophy (BMD) also was found to result from abnormality in the same dystrophin gene (Koenig, M. et al., Cell, 50:509-517(1987)).

SUMMARY

Provided herein is a general method of correcting a gene, for example a gene with many known mutations, such as a gene with mutations in many different exons which could vary from subject to subject (e.g., patient), as well as a set of tools (TALENs and gene targeting vectors) to accomplish this in, for example, the DMD locus. The key feature of this method is to modify the first exon of the gene so that it contains the entire wild-type (non-mutant) open reading frame of the desired transcript, thus converting any allele in which a mutation is downstream of the first exon into an allele that encodes the wild-type protein. One embodiment provides a nucleic acid sequence comprising 5'-ATACACTTTTCAAAATGCTT-(spacer)-AGAGGACTGTTG-TAAGTAC-3' (SEQ NOs: 5 and 6) or a sequence having 90% identity thereto. Another embodiment provides a nucleic acid sequence comprising 5'-ATATTTTACTTGTG-GCATAACGT-(spacer)-AATTAGGTAGATTGATTT-TAAATTATCAC-3' (SEQ ID NOs:9 and 10) or a sequence having 90% identity thereto. In one embodiment, the -(spacer)- is 12 to 30 random nucleotides in length.

One embodiment provides a method to treat a genetic disease or disorder caused by a genetic mutation comprising contacting a cell with one or more nucleic acids encoding a TALEN and a nucleic acid donor sequence, wherein TALEN protein is expressed in the cell and induces a site-specific double stranded DNA break in a target gene, wherein the donor sequence is a template for DNA repair resulting in a correction of the genetic mutation and provides correct gene expression, wherein the TALEN targets the first exon of the gene and results in the donor sequence to be inserted into the first exon of the target gene, so as to treat the genetic disease or disorder. In one embodiment, the cell is a fibroblast, keratinocyte, inducible pluripotent-, hematopoietic-, mesenchymal-, or embryonic stem cell, hematopoietic progeny cell (such as a T-cell or B-cell), glia and neural cell, neuroglial progenitor and stem cell, muscle cell, lung cell, pancreatic and/or liver cell and/or a cell of the reticular endothelial system. In one embodiment the TALEN is a left TALEN and further comprising a right TALEN that cooperates with the left TALEN to make the double strand break in the target gene. In another embodiment, the TALEN recognizes a nucleic acid sequence comprising 5'-ATACACTTTTCAAAATGCTT-(spacer)-AGAGGACTGTTG-TAAGTAC-3' (SEQ ID NOs:5 and 6) or a sequence having 90% identity thereto and/or a nucleic acid sequence comprising 5'-ATATTTTACTGTGGCATAACGT-(spacer)-AATTAGGTAGATTGATTTTAAATTATCAC-3 (SEQ ID NOs:9 and 10) or a sequence having 90% identity thereto. In one embodiment, the nucleic acid sequence, nucleic acid encoding the TALEN and/or the nucleic acid donor sequence is part of a vector or plasmid. In one embodiment, the target gene is a gene with a genetic alteration/mutation. In one embodiment, the target gene is DMD. In one embodiment, the genetic disease is Duchenne muscular dystrophy or Becker muscular dystrophy. The method is also applicable to any gene that has known disease-causing mutations in multiple exons, for example Cystic fibrosis transmembrane conductance regulator (CFTR; ENSG00000001626; mRNA NM_000492; protein NP_000483), dystrophy-associated fer-1-like protein(dysferlin; DYSF; ENSG00000135636; mRNA NM_001130455; protein NP_001123927), emerin (ENSG00000102119; EMD; mRNA NM_000117; protein NP_000108), LMNA gene (Lamin A/C; ENSG00000160789; mRNA NM_001257374; protein NP_001244303), TTID (Myotilin (myofibrillar titin-like protein) also known as TTID (TiTin Immunoglobulin Domain); ENSG00000120729; mRNA NM_001135940; protein NP_001129412), CAV3 (Caveolin-3 is a protein that in humans is encoded by the CAV3 gene; ENSG00000182533; mRNA NM_001234; protein NP_001225), DNAJB6 (DnaJ homolog subfamily B member 6 is a protein that in humans is encoded by the DNAJB6 gene; ENSG00000105993; mRNA NM_005494; protein NP_005485), DES (Desmin is a protein that in humans is encoded by the DES gene; ENSG00000175084; m RNA NM_001927; protein NP_001918), TNPO3 (Transportin-3 is a protein that in humans is encoded by the TNPO3 gene; ENSG00000064419; mRNA NM_001191028; protein NP_001177957), CAPN3 (Calpain-3 is a protein that in humans is encoded by the CAPN3 gene; ENSG00000092529; mRNA NM_000070; protein NP_000061), SGCG (Gamma-sarcoglycan is a protein that in humans is encoded by the SGCG gene; ENSG00000102683; mRNA NM_000231; protein NP_000222), SGCA (Alpha-sarcoglycan is a protein that in humans is encoded by the SGCA gene; ENSG00000108823; mRNA NM_000023; protein NP_000014), SGCB (Beta-sarcoglycan is a protein that in humans is encoded by the SGCB gene; ENSG00000163069; mRNA NM_000232; protein NP_000223), SGCD (Delta-sarcoglycan is a protein that in humans is encoded by the SGCD gene; ENSG00000170624; mRNA NM_000337; protein NP_000328), TCAP (Telethonin is a protein that in humans is encoded by the TCAP gene; ENSG00000173991; mRNA NM_003673; protein NP_003664), TRIM32 (Tripartite motif-containing protein 32 is a protein that in humans is encoded by the TRIM32 gene; ENSG00000119401; mRNA NM_001099679; protein NP_001093149), FKRP (Fukutin-related protein is a protein associated with congenital muscular dystrophy; NM_024301), TTN (Titin, also known as connectin, is a protein that is encoded by the TTN gene; ENSG00000155657; mRNA NM_001256850; protein NP_001243779), POMT1 (Protein O-mannosyl-transferase 1 is an enzyme that in humans is encoded by the POMT1 gene; ENSG00000130714; mRNA NM_001077365; protein NP_001070833), FKTN (Fukutin is a eukaryotic protein for the maintenance of muscle integrity, cortical histogenesis, and normal ocular development. Mutations in the fukutin gene have been shown to result in Fukuyama congenital muscular dystrophy characterised by brain malformation— one of the most common autosomal-recessive disorders in Japan. In humans this protein is encoded by the FCMD gene (also named FKTN), located on chromosome 9q31; ENSG00000106692; mRNA NM_001079802; protein NP_001073270), POMT2 (Protein O-mannosyl-transferase 2 is an enzyme that in humans is encoded by the POMT2 gene; ENSG00000009830; mRNA NM_013382; protein NP_037514), POMGNT1 (Protein O-linked-mannose beta-1,2-N-acetylglucosaminyltransferase 1 is an enzyme that in humans is encoded by the POMGNT1 gene; ENSG00000085998; mRNA NM_001243766; protein NP_001230695), PLEC1 (Plectin is a large protein (c500 kDa) found in nearly all mammalian cells which acts as a link between the three components of the cytoskeleton: actin microfilaments, microtubules and intermediate filaments; ENSG00000178209; mRNA NM_000445; protein NP_000436), ANO5 (Gene ID: 203859; anoctamin 5 (*Homo sapiens* (human)); Chromosome 11, NC_000011.10 (22192667 . . . 22283367); ENSG00000171714; NM_001142649.1→NP_001136121.1 anoctamin-5 isoform b; NM_213599.2→NP_998764.1 anoctamin-5 isoform a); HBB (Beta globin (also referred to as HBB, β-globin, haemoglobin beta, hemoglobin beta, or haemoglobin sub-unit beta) is a globin protein, which along with alpha globin (HBA), makes up the most common form of hemoglobin in adult humans, the HbA; ENSG00000244734; mRNA NM_000518; protein NP_000509); or to any other gene preselected for correction/alteration (each of the accession numbers and the information contained therein is herein incorporated by reference).

One embodiment provide a method to treat a genetic disease or disorder caused by a genetic mutation comprising a) introducing into a cell (i) a first nucleic acid encoding a first transcription activator-like (TAL) effector endonuclease monomer, (ii) a second nucleic acid encoding a second TAL effector endonuclease monomer, and (iii) and a donor sequence, wherein each of said first and second TAL effector endonuclease monomers comprises a plurality of TAL effector repeat sequences and a FokI endonuclease domain, wherein each of said plurality of TAL effector repeat sequences comprises a repeat-variable diresidue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences, wherein said donor sequence comprises comprises a complete coding region for the target gene; and (b) culturing the cell under conditions in which the first and second TAL effector endonuclease monomers are expressed, wherein the TALEN targets the first exon of the gene and results the donor sequence to be inserted into the first exon of the target gene, so as to result in expression of a wildtype open reading frame of the target gene, and administrating an effective amount of cells to a subject in need thereof so as to treat the genetic disease or disorder.

Another embodiment provides a method to treat a genetic disease or disorder caused by a genetic mutation comprising a) introducing into a cell (i) a first nucleic acid encoding a first transcription activator-like (TAL) effector endonuclease monomer, (ii) a second nucleic acid encoding a second TAL effector endonuclease monomer, and (iii) and a donor sequence, wherein each of said first and second TAL effector endonuclease monomers comprises a plurality of TAL effector repeat sequences and a FokI endonuclease domain, wherein each of said plurality of TAL effector repeat sequences comprises a repeat-variable diresidue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences, wherein said donor sequence comprises homology to the target at least at the 5' and 3's ends of the target sequence and the preselected genetic alteration and is a template for DNA repair resulting in a correction of the genetic mutation; and (b) culturing the cell under conditions in which the first and second TAL effector endonuclease monomers are expressed, wherein the TALEN targets the first exon of the gene and results the donor sequence to be inserted into the first exon of the target gene, so as to correct the mutation and restores correct gene expression.

One embodiment provides a vector or plasmid comprising one or more sequences described herein. Another embodiment provides an isolated host cell comprising one or more of the exogenous sequences described herein or the proteins expressed from such sequences. One embodiment provides a transfected cell line comprising one or more sequences described herein or the proteins expressed from such sequences.

DETAILED DESCRIPTION

Figure 1:
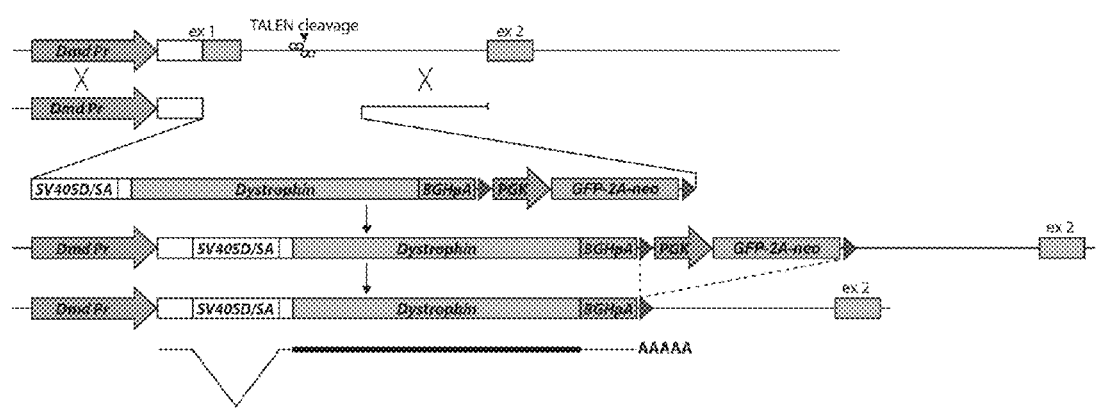
FIG. 1. Approach 1: TALEN-mediated targeting of DMD locus. (A) Strategy for correction through DMD ex1 modification. (B) PCR across the 5' and 3' junctions using primers outside of the targeting arms was performed on clones C3, C10, C20, C29, derived from iPS cell line 12-017-B1 by TALEN-mediated gene targeting of exon 1. PCR primers are shown as red arrows on the left panel. iPS cells that had received only the targeting vector and no TALENs gave sparse G418-resistant colonies that were negative for site-specific integration PCRs.
Figure 1:
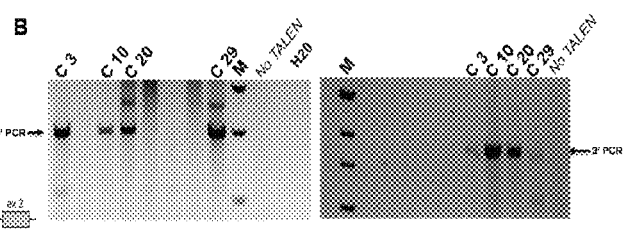
Figure 2:
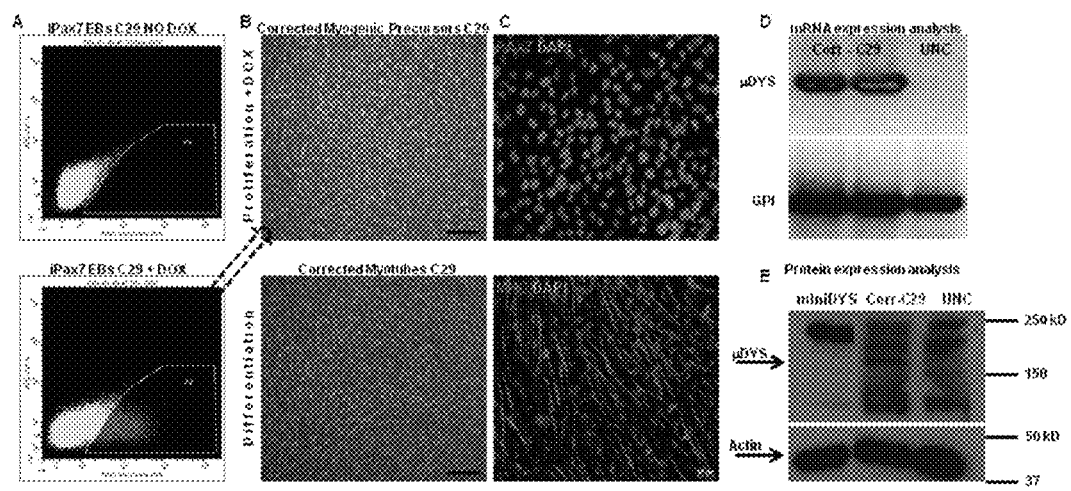
FIG. 2. In vitro characterization of skeletal myogenic progenitors from gene-corrected DMD-iPS cells 'clone C29.' (A) FACS purification of iPAX7 Cherry+ myogenic precursors. (B) Phase-contrast images of monolayers under proliferation (top) and differentiation (bottom) culture conditions. (C) Immunofluorescence staining for PAX7 (red), and MyHC (red) in proliferation and differentiation condition, respectively. DAPI in blue. (D) mRNA analysis indicates expression of μDYS in corrected myotubes for clone C29. UNC is for uncorrected myotubes. GPI was used as house-keeping gene. (E) Immunoblotting with anti-DYS antibodies confirms the presence of 170 kDa mDYS only in corrected myotubes (Corr-C29). Mini-DYS protein extraction was used as a positive control. Control uncorrected cells are labeled as UNC. Actin was used as house-keeping protein.

As it is not feasible to tailor-make genome engineering tools for each mutation in many patient sets, a standardized genome engineering toolkit that can repair any allele by targeting, for example, the full length open reading frame (ORF) of a gene into exon 1 or other pre-selected exon (an example of such is the full length DMD ORF into exon 1 of the dystrophin gene) such that said exon will be modified to contain the entire remainder of the ORF that would otherwise be downstream of said exon.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

A "control" subject is a subject having the same characteristics as a test subject, such as a similar type of disease, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. However, the definitions of "disease" and "disorder" as described above are not meant to supersede the definitions or common usage related to specific addictive diseases or disorders.

A disease, condition, or disorder is "alleviated" if the severity of a symptom of the disease or disorder, the frequency with which such a symptom is experienced by a patient, or both, are reduced.

As used herein, an "effective amount" means an amount sufficient to produce a selected effect, such as alleviating symptoms of a disease or disorder.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

The term "specifically binds," as used herein, is meant a molecule which recognizes and binds a specific molecule, but does not substantially recognize or bind other molecules in a sample.

The term "symptom," as used herein, refers to any morbid phenomenon or departure from the normal in structure, function, or sensation, experienced by the patient and indicative of disease.

As used herein, the term "treating" may include prophylaxis of the specific disease, disorder, or condition, or alleviation of the symptoms associated with a specific disease, disorder or condition and/or preventing or eliminating the symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

A "therapeutic" treatment is a treatment administered to a subject who exhibits symptoms of pathology for the purpose of diminishing or eliminating those symptoms.

A "therapeutically effective amount" of a compound is that amount of compound which is sufficient to provide a beneficial effect to the subject to which the compound is administered.

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, the term "nucleic acid" encompasses RNA as well as single, double and triple stranded DNA and cDNA. Furthermore, the terms, "nucleic acid," "DNA," "RNA" and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention. By "nucleic acid" is also meant any nucleic acid, whether composed of deoxyribonucleo sides or ribonucleo sides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using, for example, the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The terms "comprises," "comprising," and the like can have the meaning ascribed to them in U.S. Patent Law and can mean "includes," "including" and the like. As used herein, "including" or "includes" or the like means including, without limitation.

TALENS

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage for genome editing in situ. Transcription activator-like effectors (TALEs) are proteins that bind DNA in a sequence specific way. By fusing such a TALE to a nuclease (e.g., FokI endonuclease) a highly specific DNA "scissor" is made (these molecules can be engineered to bind any DNA sequence). The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA.

TAL effectors are proteins secreted by Xanthomonas bacteria. The DNA binding domain contains a highly conserved 33-34 amino acid sequence with the exception of the 12th and 13th amino acids. These two locations are highly variable (Repeat Variable Diresidue (RVD)) and show a strong correlation with specific nucleotide recognition. This simple relationship between amino acid sequence and DNA recognition has allowed for the engineering of specific DNA binding domains by selecting a combination of repeat segments containing the appropriate RVDs.

The non-specific DNA cleavage domain from the end of the FokI endonuclease can be used to construct hybrid nucleases that are active in a yeast assay. These reagents are also active in plant cells and in animal cells. Initial TALEN studies used the wild-type FokI cleavage domain, but subsequent TALEN studies also used FokI cleavage domain variants with mutations designed to improve cleavage specificity and cleavage activity. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Artificial gene synthesis can be problematic because of improper annealing of the repetitive sequence found in the TALE binding domain. One solution to this is to use a publicly available software program (DNAWorks) to calculate oligonucleotides suitable for assembly in a two step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB) and optionally inserting a cargo/preselected gene, which cells respond to with repair mechanisms. In this manner, they can be used to correct mutations in the genome which, for example, cause disease.

Vectors and Nucleic Acids

A variety of nucleic acids may be introduced into cells to obtain expression of a gene. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

Nucleic acid sequences can be operably linked to a regulatory region such as a promoter. Regulatory regions can be from any species. As used herein, operably linked refers to positioning of a regulatory region relative to a nucleic acid sequence in such a way as to permit or facilitate transcription of the target nucleic acid. Any type of promoter can be operably linked to a nucleic acid sequence. Examples of promoters include, without limitation, tissue-specific promoters, constitutive promoters, and promoters responsive or unresponsive to a particular stimulus (e.g., inducible promoters).

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

Nucleic acid constructs can be introduced into cells of any type using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

Therapeutic Uses

TALEN-based gene correction has many clinical and preclinical (e.g., research) applications. For example, TALEN-based gene correction can used to correct genes in which mutations lead to disease. For example, any disease characterized by small base alterations including insertions, deletions and mutations such as, but not restricted to, muscular dystrophy. The gene may have more than one mutation. These mutations can be located in one region of the gene (e.g., one exon) or spread across the gene. The mutations can also vary from subject to subject (e.g., person to person). Using TALEN based technology, as described herein, the gene is corrected via insertion of a complete coding region for the gene upstream of the mutations, such as in exon 1 of the gene. Via this method and with these tools, all mutation are corrected in all patients.

In one embodiment, the disease is muscular dystrophy. DMD has 79 exons, and is spread across megabases of the human genome. Most of these exons can have disease-causing mutations. Described herein is the correction any mutation downstream of exon 1, by insertion of the complete coding sequence of the DMD ORF into exon 1, followed by a transcriptional stop signal. Because this would make a transcript without any exons, which might be unstable, it was further elected to include a synthetic exon upstream of the ORF (FIG. 1). With such a tool, the DMD locus can be corrected in cells from Duchenne muscular dystrophy patients.

To target this construct into the DMD locus, TALENs were designed that would generate double strand breaks just downstream of DMD exon I. By using TALENS, one obviates the shortcomings associated with the genetic correction by random integration of mini-versions of DMD, which is a very large (12 kb) open reading frame.

Cells to be modified by TALEN-based gene correction can be obtained from the patient or from a donor. The cells can be of any type, such as fibroblast cells, keratinocytes, inducible pluripotent-, hematopoietic-, mesenchymal-, and embryonic stem cells, hematopoietic progeny cells, such as T-cells, B-cells, glia and neurons, neuroglial progenitor and stem cells, muscle cells, lung cells, pancreatic and liver cells and/or cells of the reticular endothelial system. Once modified by TALEN-based gene correction, the cells can be expanded and/or administered to a patient to treat the disease.

Cells can be administered to a subject by a variety of methods available to the art, including but not limited to localized injection, catheter administration, systemic injection, intraperitoneal injection, parenteral administration, intra-arterial injection, intravenous injection, transvascular injection, intramuscular injection, surgical injection into a tissue of interest or via direct application to tissue surfaces (e.g., during surgery or on a wound). For example, cells can be administered either peripherally or locally through the circulatory system.

Matrices can be used to deliver cells of the present invention to specific anatomic sites, where particular growth factors may or may not be incorporated into the matrix, or encoded on plasmids incorporated into the matrix for uptake by the cells, can be used to direct the growth of the initial cell population. Plasmid DNA encoding cytokines, growth factors, or hormones can be trapped within a polymer gene-activated matrix carrier. The biodegradable polymer is then implanted near the site where treatment is desired.

For the purposes described herein, either autologous, allogeneic or xeongenic cells of the present invention can be administered to a patient by direct injection to a preselected site, systemically, on or around the surface of an acceptable matrix, or in combination with a pharmaceutically acceptable carrier.

The quantity of cells to be administered will vary for the subject being treated. In one embodiment, between about $10^4$ to about $10^8$, such as about $10^5$ to about $10^7$ and including, about $3 \times 10^7$ cells and can be administered to a human subject. However, the precise determination of what would be considered an effective dose may be based on factors individual to each patient, including their size, age, disease or injury, amount of damage, amount of time since the damage occurred and factors associated with the mode of delivery (direct injection—lower doses, intravenous—higher doses). Dosages can be readily ascertained by those skilled in the art from this disclosure and the knowledge in the art.

Additionally, nucleic acid constructs or proteins can be injected locally or systemically into a subject, with, for example, a pharmaceutically acceptable carrier.

When administering a composition of the present invention, it can generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used should be compatible with the cells.

Growth/Expansion of Cells

Cells to be modified by TALEN-based gene correction can be obtained from the patient or from a donor. The cells can be of any type, such as muscle cells, or induced pluripotent cells. Once modified by TALEN-based gene correction, the cells can be expanded and/or administered to a patient to treat the disease.

The cells can be cultured in culture medium that is established in the art and commercially available from the American Type Culture Collection (ATCC), Invitrogen and other companies. Such media include, but are not limited to, mTESR, TESR-E8, Dulbecco's Modified Eagle's Medium (DMEM), DMEM F12 medium, Eagle's Minimum Essential Medium, F-12K medium, Iscove's Modified Dulbecco's Medium, Knockout D-MEM, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are needed for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements (including, but not limited to, KnockOut Serum Replacement (KSR, Invitrogen)), and bovine embryonic fluid. It is understood that sera can be heat-inactivated at 55-65° C. if deemed needed to inactivate components of the complement cascade. Modulation of serum concentrations, or withdrawal of serum from the culture medium can also be used to promote survival of one or more desired cell types. In one embodiment, the cells are cultured in the presence of FBS/or serum specific for the species cell type. For example, cells can be isolated and/or expanded with total serum (e.g., FBS) or serum replacement concentrations of about 0.5% to about 5% or greater including about 5% to about 15% or greater, such as about 20%, about 25% or about 30%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution™ (HBSS), Earle's Salt Solution™, antioxidant supplements, MCDB-201™ supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination.

Typically, antibiotics or anti-mycotic compounds used are mixtures of penicillin/streptomycin, but can also include, but are not limited to, amphotericin (Fungizone™) ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel™, thrombospondin, and/or vitronectin.

Cells can be cultured at different densities, e.g., cells can be seeded or maintained in the culture dish at different densities. For example, at densities, including, but not limited to, densities of less than about 2000 cells/well of a 12-well plate (for example, 12-well flat-bottom growth area: 3.8 cm2 well volume: 6.0 ml or well ID×depth (mm) 22.1×17.5; well capacity (ml) 6.5, growth area (cm2) 3.8), including less than about 1500 cells/well of a 12-well plate, less than about 1,000 cells/well of a 12-well plate, less than about 500 cells/well of a 12-well plate, or less than about 200 cells/well of a 12-well plate. The cells can also be seeded or maintained at higher densities, for example, great than about 2,000 cells/well of a 12-well plate, greater than about 2,500 cells/well of a 12-well plate, greater than about 3,000 cells/well of a 12-well plate, greater than about 3,500 cells/well of a 12-well plate, greater than about 4,000 cells/well of a 12-well plate, greater than about 4,500 cells/well of a 12-well plate, greater than about 5,000 cells/well of a 12-well plate, greater than about 5,500 cells/well of a 12-well plate, greater than about 6,000 cells/well of a 12-well plate, greater than about 6,500 cells/well of a 12-well plate, greater than about 7,000 cells/well of a 12-well plate, greater than about 7,500 cells/well of a 12-well plate or greater than about 8,000 cells/well of a 12-well plate.

EXAMPLES

The following example is provided in order to demonstrate and further illustrate certain embodiments and aspects of the present invention and is not to be construed as limiting the scope thereof.

Example 1

Genetic Correction of DMD Induced Pluripotent Stem (iPS) Cells

To enable genome engineering, site-specific recombination based on chimeric DNA-binding nucleases, transcription effector-like nucleases (TALENs: 33) was used.

Results/Discussion

A TALEN pair was designed and tested that targets in the vicinity exon 1 of the dystrophin gene (exon 1 defined as the first exon of the main muscle-specific Dp427m isoform of dystrophin). A 2 kb upstream targeting arm covering the promoter/exon 1 junction, and downstream arm of approximately 5 kb were isolated by PCR. Between these arms the full-length dystrophin ORF was inserted followed by a floxed selection cassette (PGKneo-GFP) (FIG. 1A). DTA negative selection cassettes can be cloned outside of the homologous regions to kill cells that randomly integrate the construct, however this is not essential for this targeting (FIG. 1).

After nucleofection, GFP$^+$ iPS cell clones that are resistant to G418 were expanded and screened by PCR, as shown in FIG. 1B. Karyotypically normal clones can be nucleofected with cre to eliminate the positive selection cassette and GFP-negative clones were identified and expanded. Dystrophin expression can be confirmed by in vitro and in vivo studies. Suitable clones will be further analyzed by Southern blotting.

Materials and Methods

Cell Culture and Differentiation Protocol

Human DMD induced pluripotent stem cells (DMD-hiPSCs) were maintained in feeder free conditions using mTeSR medium (STEMCELL Technologies) on human ESC qualified Matrigel (BD Biosciences) coated plates. hiPSCs were differentiated as EBs, as previously reported (Darabi R, Cell Stem Cell 2012).

Generation of Human Micro-Dystrophin Targeting Vector

The targeting vector was generated using the pBSK plasmid. In this backbone plasmid, two resistance gene cassettes were cloned, the positive selection marker GFP-2A-neo and the negative selection marker herpes simplex virus thymidine kinase (HSV-tk) gene, driven respectively by hEF1-elF4g and MC1 promoters. The positive selection marker (promoter GFP-2A-neo) was flanked by two loxP sequences. Upstream of the negative selection marker the left arm sequence was cloned, homologous to the 5' untranslated region (5'-UTR) of the DMD locus, and a chimeric intron sequence. Downstream of the GFP-2A-neo cassette, the right arm sequence was cloned, homologous to the first intron of the DMD. Arms were amplified from a healthy DNA donor using specific primers forward 5'-AGCAG-GAAAACATGTCCCAT-3' (SEQ ID NO:1) and reverse 5'-TTTGAAAAGTGTATATCAAGGC-3' (SEQ ID NO:2) for the left arm (830 bp), and forward 5'-AGTAGTTTG-CAAAGAAGCATAA-3' (SEQ ID NO:3) and reverse 5'-GAGATAAACTCCCATCTCTT-3' (SEQ ID NO:4) for the right arm (828 bp). PCR was performed using high fidelity Taq (Roche) on 100 ug of genomic DNA using the following cycling parameters: 30 cycles of 30 s at 95° C., 30 s at 57° C. and 1 min at 72° C. PCR products were clone into Pcr2.1 topo cloning kit (Invitrogen) and sequenced (nucleotide sequence of arms are present in supplementary material). In the targeting vector, the gateway cloning cassette sequence was cloned using NoI (New England Biolabs) site. The μH2-hDystrophin was generated using the full-length human dystrophin cDNA in the Gateway entry vector pENTR223.1 (NM_004006) that was obtained from The ORFeome Collaboration. The entry vector was N-terminally FLAG-tagged via PCR using primers with overhangs encoding the tag. The μH2-hDystrophin-Δ4-23 was built by deletion as previously described (Imai et al., 1991). Briefly, PCR primers were designed such that they amplified the entire plasmid except the region being deleted, namely spectrin-like repeats 4-23. These linear PCR products were then circularized via the addition of T4 polynucleotide kinase and T4 DNA ligase (New England Biolabs) and sequence verified. A second round of PCR and circularization was performed to delete the C-terminus. All PCRs were performed using PfuII Ultra HS polymerase (Stratagene). Finally, the human micro-dystrophin targeting vector was generated using the Gateway® Vector Conversion System with One Shot® ccdB Survival Cells (Invitrogen™)

Construction of TALEN Expression Vectors.

TALEN pairs (TALEN 40 and TALEN 52) targeting exon 1 of the DMD locus were generated by Golden Gate TALEN and TAL Effector Kit, as described (Cermak T, 2011). TALEN 40 target nucleotide sequence for the 5'-strand is 5'-ATACACTTTTCAAAATGCTT-(spacer)-AGAGGACT-GTTGTAAGTAC-3' (SEQ ID NOs: 5 and 6). The repeat-variable diresidue (RVD) are for TALEN-40-5': NI NG NI HD NI UD NG NG NG NG HD NI NI NI NI NG NN HD NG NG (SEQ ID NO:7); and for TALEN-40-3': NN NG NI HD NG NG NI HD NI NI HD NI NN NG HD HD NG HD NG (SEQ ID NO:8). TALEN 52 target nucleotide sequence for the 5'-strand is ATATTTTACTGTGGCATAACGT-(spacer)-AATTAGGTAGATTGATTTTAAATTATCAC (SEQ ID NOs:9 and 10). The RVDs are for TALEN-52-5':NI NG NI NG NG NG NG NI HD NG NN NG NN NN HD NI NG NI NI HD NN NG (SEQ ID NO:11): and for TALEN-52-3': NN NG NN NI NG NI NI NG NG NG NI NI NI NI NG HD NI NI NG HD NG NI HD HD NG NI NI NG NG (SEQ ID NO:12).

Generation of Corrected DMD B1 iPSCs Using TALENs.

For gene targeting of the MID locus, 2.2×10⁵ iPS cells were nucleofected with 2 μg of TALENs (left5' and right3') and 3 μg of micro-dystrophin targeting vector using Nucleofector 96-well Shuttle (program CD-100) (Lonza). After nucleofection, cells were plated on matrigel and 72 h later iPS clones were selected with Geneticin (G418, Sigma) (50 ug/ml). At day 10 following nucleofection, resistant clones were grown in presence of Ganciclovir for 5 days (2 μM/ml). This negative selection was used to eliminate the iPS clones in which the targeting vector was still present as episomal plasmid, and was not integrated by homologous recombination. Genomic DNA was extracted from mock-nucleofected and selected iPS clones (DNA extraction kit, Invitrogen) and the DNA samples were subjected to PCR for effective gene targeting at the DMD locus using specific primers for the 5' and 3' regions where the targeting vector was recombined. For the analysis of the 5'-region of the DMD locus the primer forward (P1=5'-AATTGGCACCA-GAGAAATGG-3'; SEQ ID NO: 13) was designed outside of the targeting region and the reverse primer (P2=5'-TCTC-GACAAGCCCAGTTTCT-3'; SEQ ID NO: 14) was designed to anneal the chimeric intron present only into the genome of corrected clones. The PCR product is 1071 bp (FIG. 1C). The PCR reaction was performed as following: after a 3-min denaturation step at 95° C., the samples were subjected to 35 cycles consisting of 30 s at 95° C., 30 s at 55° C. and 1 min at 72° C. The reactions were terminated by a final elongation period of 10 min at 72° C.

For the analysis of 3'-region the forward primer (P3=5'-TCTTTTAATGATCTAGAACCGG-3'; SEQ ID NO: 15) was designed within the Neo$^R$ gene and the reverse primer (P4=5'-AATCCTACAGGGCATGTCCC-3'; SEQ ID NO: 16) was generated to bind the 3' region outside the recombination site (FIG. 1C). PCR analysis was performed with 0.4 μM of these primers, 0.1 mM of dNTP, 1× Colorless GoTaq Flexi buffer, 1.25 mM $MgCl_2$ and 2.5 units of GoTaq DNA polymerase (all from Promega). The PCR reaction consisted in denaturation step of 3 minutes follow 35 cycles of 30 s at 95° C., 30 s at 62° C. and 1.3 min at 72° C. The reactions were terminated by a final elongation period of 10 min at 72° C.

RNA Extraction and mRNA Analysis.

RNA was isolated from EB-derived myogenic cells using TRIzol reagent (Life Technology). 1 μg of total RNA was retro transcribed using the ThermoScript™ Reverse Transcriptase kit (Life Technology). To confirm μH2-hDystrophin expression in corrected iPSCs was performed a reverse transcriptase-PCR (RT-PCR) analysis of mRNA. Primers were design for uH2-hDystrophin gene (F: 5'-TTCTAAGTTTGGGAAGCAGCA-3' (SEQ ID NO: 17) and R: GGTCTGGCCTATGACTATGGA (SEQ ID NO: 18). As house-keeping gene was used; primers for GPI F: 5'-GCAGTGGCGAAGCACTTT-3' (SEQ ID NO: 19) and R.: 5'-ACAATAGAGTTGGTTGGGGG-3' (SEQ ID NO: 20)). The PCR was performed as follows: 35 cycles of 30 s at 95° C., 30 s at 58° C. and 30 min at 72° C. The reactions were terminated by a final elongation period of 10 min at 72° C.

Complete Sequence of Targeting Vector:
Seq:

```
LOCUS        GS52375  pBSK-GS52375   9068 bp    DNA

FEATURES             Location/Qualifiers
     CDS             21 . . . 327
                     /gene = "f1 origin"
     misc_feature    600 . . . 643
                     /gene = "T7/M13F"
     CDS             656 . . . 6854
                     /gene = "GS52375"
     misc_feature    complement (6879 . . . 6935)
                     /gene = "T3/M13R"
     misc_feature    7265 . . . 7932
                     /gene = "pUC origin"
```

-continued

```
CDS             complement (8083 . . . 8940)
                /gene = "Ampcillin"
```

BASE COUNT    2238 a   2268 c   2320 g   2242 t

ORIGIN
(SEQ ID NO: 21)

```
   1 CTGACGCGCC CTGTAGCGGC GCATTAAGCG CGGCGGGTGT GGTGGTTACG CGCAGCGTGA
  61 CCGCTACACT TGCCAGCGCC CTAGCGCCCG CTCCTTTCGC TTTCTTCCCT TCCTTTCTCG
 121 CCACGTTCGC CGGCTTTCCC CGTCAAGCTC TAAATCGGGG GCTCCCTTTA GGGTTCCGAT
 181 TTAGTGCTTT ACGGCACCTC GACCCCAAAA AACTTGATTA GGGTGATGGT TCACGTAGTG
 241 GGCCATCGCC CTGATAGACG GTTTTTCGCC CTTTGACGTT GGAGTCCACG TTCTTTAATA
 301 GTGGACTCTT GTTCCAAACT GGAACAACAC TCAACCCTAT CTCGGTCTAT TCTTTTGATT
 361 TATAAGGGAT TTTGCCGATT TCGGCCTATT GGTTAAAAAA TGAGCTGATT TAACAAAAAT
 421 TTAACGCGAA TTTTAACAAA ATATTAACGC TTACAATTTG CCATTCGCCA TTCAGGCTGC
 481 GCAACTGTTG GGAAGGGCGA TCGGTGCGGG CCTCTTCGCT ATTACGCCAG CTGGCGAAAG
 541 GGGGATGTGC TGCAAGGCGA TTAAGTTGGG TAACGCCAGG GTTTTCCCAG TCACGACGTT
 601 GTAAAACGAC GGCCAGTGAA TTGTAATACG ACTCACTATA GGGCGACCCA AGCTTTCTAG
 661 AGTCGAGCAG TGTGGTTTTC AAGAGGAAGC AAAAAGCCTC TCCACCCAGG CCTGGAATGT
 721 TTCCACCCAA TGTCGAGCAG TGTGGTTTTG CAAGAGGAAG CAAAAAGCCT CTCCACCCAG
 781 GCCTGGAATG TTTCCACCCA ATGTCGAGCA AACCCCGCCC AGCGTCTTGT CATTGGCGAA
 841 TTCGAACACG CAGATGCAGT CGGGGCGGCG CGGTCCCAGG TCCACTTCGC ATATTAAGGT
 901 GACGCGTGTG GCCTCGAACA CCGAGCGACC CTGCAGCGAC CCGCTTAACA GCGTCAACAG
 961 CGTGCCGCAG ATCTTGGTGG CGTGAAACTC CCGCACCTCT TCGGCCAGCG CCTTGTAGAA
1021 GCGCGTATGG CTTCGTACCC CGGCCATCAG CACGCGTCTG CGTTCGACCA GGCTGCGCGT
1081 TCTCGCGGCC ATAGCAACCG ACGTACGGCG TTGCGCCCTC GCCGGCAGCA AGAAGCCACG
1141 GAAGTCCGCC CGGAGCAGAA AATGCCCACG CTACTGCGGG TTTATATAGA CGGTCCCCAC
1201 GGGATGGGGA AAACCACCAC CACGCAACTG CTGGTGGCCC TGGGTTCGCG CGACGATATC
1261 GTCTACGTAC CCGAGCCGAT GACTTACTGG CGGGTGCTGG GGCTTCCGA DACAATCGCG
1321 AACATCTACA CCACACAACA CCGCCTTGAC CAGGGTGAGA TATCGGCCGG GGACGCGGCG
1381 GTGGTAATGA CAAGCGCCCA GATAACAATG GGCATGCCTT ATGCCGTGAC CGACGCCGTT
1441 CTGGCTCCTC ATATCGGGGG GGAGGCTGGG AGCTCACATG CCCCGCCCCC GGCCCTCACC
1501 CTCATCTTCG ACCGCCATCC CATCGCCGCC TCCTGTGCT ACCCGGCCGC GCGATACCTT
1561 ATGGGCAGCA TGACCCCCCA GGCCGTGCTG GCGTTCGTGG CCCTCATCCC GCCGACCTTG
1621 CCCGGCACAA ACATCGTGTT GGGGGCCCTT CCGGAGGACA GACACATCGA CCGCCTGGCC
1681 AAACGCCAGC GCCCCGGCGA GCGGCTTGAC CTGGCTATGC TGGCCGCGAT TCGCCGCGTT
1741 TACGGGCTGC TTGCCAATAC GGTGCGGTAT CTGCAGGGCG GCGGGTCGTG GCGGGAGGAT
1801 TGGGGACAGC TTTCGGGGAC GGCCGTGCCG CCCCAGGGTG CCGAGCCCCA GAGCAACGCG
1861 GGCCCACGAC CCCATATCGG GGACACGTTA TTTACCCTGT TCGGGCCCC CGAGTTGCTG
1921 GCCCCCAACG GCGACCTGTA CAACGTGTTT GCCTGGGCCT TGGACGTCTT GGCCAAACGC
1981 CTCCGTCCCA TGCACGTCTT TATCCTGGAT TACGACCAAT CGCCCGCCGG CTGCCGGGAC
2041 GCCCTGCTGC AACTTACCTC CGGGATGATC CAGACCCACG TCACCACCCC AGGCTCCATA
2101 CCGACGATCT GCGACCTGGC GCGCACGTTT GCCCGGGAGA TGGGGAGGC TAACTGAAAC
2161 ACGGAAGGAG ACAATACCGG AAGGAACCCG CGCTATGACG GCAATAAAAA GACAGAACAG
```

-continued

```
2221 CATGATAAGA TACATTGATG AGTTTGGACA AACCACAACT AGAATGCAGT GATAACAATG

2281 CTTTATTTGT GAAATTTGTG ATGCTATTGC TTTATTTGTG AAATTTGTGA TGCTATTGCT

2341 TTATTTGTAA CCATTATAAG CTGCAATAAA CAAGTTAACA ACAACAATTG CATTCATTTT

2401 ATGTTTCAGG TTCAGGGGGA GGTGTGGGAG GTTTTTTAAA GCAAGTAAAA CCTCTACAAA

2461 TGTGGTAGAT CCATTTAAAT GTTAATTAAA GCAGGAAAAC ATGTCCCATG AGACCTATAC

2521 ACACACACAT TCTGCCTTCA GAATTCAGCT GCTGCATTCT GCTGCTGCTT CTCTTATTCA

2581 GACTGTTGGC ATCATCAATA CATAACTTTT GATTGAATCC CAAGGGGAAA AATAACTTT

2641 GGTAGACAGT GGATACATAA CAAATGCATG GATTATTCTG GGCATTCCTT TTTATTTGGT

2701 AGAGTGAAAT TTTTGGTGTT GTTGAGAGGA TAAAAAAGGC ATTTAAAAGT CAATTTTGAA

2761 TCCGGATTTT CTGCTCTGTT AATAAATTCA CATGAAAGTT ACAGAAAGTA TTGTTATGCT

2821 TTTGTACTGA ATAGTTTTTG TGTTTAGAAG GCTTTAAAAG CAAGTACTAT GTCCACTGTG

2881 CTATTCTGGT TTGGATATTA ATCAGAACAC AGTTGAGCAT TGTTTGAATT CACAGAGCTT

2941 GCCATGCTGG AAGCACAACC TTATATGTAG TGACCATGGA CAGTCCTATT ATGGGAAACC

3001 AACTTGAGAG AGAAGGCGGG TCACTTGCTT GTGCGCAGGT CCTGGAATTT GAAATATCCG

3061 GGGGCCTCTA CAGAATCCTG GCATCAGTTA CTGTGTTGAC TCACTCAGTG TTGGGATCAC

3121 TCACTTTCCC CCTACAGGAC TCAGATCTGG GAGGCAATTA CCTTCGGAGA AAAACGAATA

3181 GGAAAAACTG AAGTGTTACT TTTTTTAAAG CTGCTGAAGT TTGTTGGTTT CTCATTGTTT

3241 TTAAGCCTAC TGGAGCAATA AAGTTTGAAG AACTTTTACC AGGTTTTTTT TATCGCTGCC

3301 TTGATATACA CTTTTCAAAG TAAGTATCAA GGTTACAAGA CAGGTTTAAG GAGACCAATA

3361 GAAACTGGGC TTGTCGAGAC AGAGAAGACT CTTGCGTTTC TGATAGGCAC CTATTGGTCT

3421 TACTGACATC CACTTTGCCT TTCTCTCCAC AGCTCGAGTC TAGCGGCCGC CAGCATGATA

3481 AGATACATTG ATGAGTTTGG ACAAACCACA ACTAGAATGC AGTGAAAAAA ATGCTTTATT

3541 TGTGAAATTT GTGATGCTAT TGCTTTATTT GTGAAATTTG TGATGCTATT GCTTTATTTG

3601 TAACCATTAT AAGCTGCAAT AAACAAGTTA ACAACAACAA TTGCATTCAT TTTATGTTTC

3661 AGGTTCAGGG GGAGGTGTGG GAGGTTTTTT AAAGCAAGTA AAACCTCTAC AAATGTGGTA

3721 GATCCATTTA AATGTTAATT AAATAACTTC GTATAGCATA CATTATACGA AGTTATGGAT

3781 CTGCGATCGC TCCGGTGCCC GTCAGTGGGC AGAGCGCACA TCGCCCACAG TCCCGAGAA

3841 GTTGGGGGGA GGGGTCGGCA ATTGAACCGG TGCCTAGAGA AGGTGGCGCG GGGTAAACTG

3901 GGAAAGTGAT GTCGTGTACT GGCTCCGCCT TTTTCCCGAG GGTGGGGGAG AACCGTATAT

3961 AAGTGCAGTA GTCGCCGTGA ACGTTCTTTT TCGCAACGGG TTTGCCGCCA GAACACAGCT

4021 GGTGGGTAGG GATGAGGGAG GGAGGGGCAT TGTGATGTAC AGGGCTGCTC TGTGAGATCA

4081 AGGGTCTCTT AAGGGTGGGA GCTGGGGCAG GGACTACGAG AGCAGCCAGA TGGGCTGAAA

4141 GTGGAACTCA AGGGGTTTCT GGCACCTACC TACCTGCTTC CCGCTGGGGG GTGGGGAGTT

4201 GGCCCAGAGT CTTAAGATTG GGCAGGGTG GAGAGGTGGG CTCTTCCTGC TTCCCACTCA

4261 TCTTATAGCT TTCTTTCCCC AGATCCGAAT TCGAGATCCA AACCAAGGAG GAAAGGATAT

4321 CACAGAGGAG ACCATGGTGA GCAAGGGCGA GGAGCTGTTC ACCGGGGTGG TGCCCATCCT

4381 GGTCGAGCTG GACGGCGACG TAAACGGCCA CAAGTTCAGC GTGTCTGGCG AGGGCGAGGG

4441 CGATGCCACC TACGGCAAGC TGACCCTGAA GTTCATCTGC ACCACCGGCA AGCTGCCCGT

4501 GCCCTGGCCC ACCCTCGTGA CCACCCTGAC CTACGGCGTG CAGTGCTTCA GCCGCTACCC

4561 CGACCACATG AAGCAGCACG ACTTCTTCAA GTCCGCCATG CCCGAAGGCT ACGTCCAGGA

4621 GCGCACCATC TTCTTCAAGG ACGACGGCAA CTACAAGACC CGCGCCGAGG TGAAGTTCGA
```

```
4681 GGGCGACACC CTGGTGAACC GCATCGAGCT GAAGGGCATC GACTTCAAGG AGGACGGCAA
4741 CATCCTGGGG CACAAGCTGG AGTACAACTA CAACAGCCAC AACGTCTATA TCATGGCCGA
4801 CAAGCAGAAG AACGGCATCA AGGCGAACTT CAAGATCCGC CACAACATCG AGGACGGCAG
4861 CGTGCAGCTC GCCGACCACT ACCAGCAGAA CACCCCCATC GGCGACGGCC CCGTGCTGCT
4921 GCCCGACAAC CACTACCTGA GCACCCAGTC CGCCCTGAGC AAAGACCCCA ACGAGAAGCG
4981 CGATCACATG GTCCTGCTGG AGTTCGTGAC CGCCGCCGGG ATCACTCTCG GCATGGACGA
5041 GCTGTACAAG GGAAGAGCCG AGGGCAGGGG AAGTCTTCTA ACATGCGGGG ACGTGGAGGA
5101 AAATCCCGGG CCCGGAATCG AACAAGACGG CCTCCATGCT GGCAGTCCCG CAGCTTGGGT
5161 CGAACGCTTG TTCGGGTACG ACTGGGCCCA GCAGACCATC GGATGTAGCG ATGCGGCCGT
5221 GTTCCGTCTA AGCGCTCAAG GCCGGCCCGT GCTGTTCGTG AAGACCGACC TGAGCGGCGC
5281 CCTGAACGAG CTTCAAGACG AGGCTGCCCG CCTGAGCTGG CTGGCCACCA CCGGCGTACC
5341 CTGCGCCGCT GTGTTGGATG TTGTGACCGA AGCCGGCCGG GACTGGCTGC TGCTGGGCGA
5401 GGTCCCTGGC CAGGATCTGC TGAGCAGCCA CCTTGCCCCC GCTGAGAAGG TTTCTATCAT
5461 GGCCGATGCA ATGCGGCGCC TGCACACCCT GGACCCCGCT ACCTGCCCCT TCGACCACCA
5521 GGCTAAGCAT CGGATCGAGC GTGCTCGGAC CCGCATGGAG GCCGGCCTGG TGGACCAGGA
5581 CGACCTGGAC GAGGAGCATC AGGGCCTGGC CCCCGCTGAA CTGTTCGCCC GACTGAAAGC
5641 CCGCATGCCG GACGGTGAGG ACCTGGTTGT CACACACGGA GATGCCTGCC TCCCTAACAT
5701 CATGGTCGAG AATGGCCGCT TCTCCGGCTT CATCGACTGC GGTCGCCTAG GAGTTGCCGA
5761 CCGCTACCAG GACATCGCCC TGGCCACCCG CGACATCGCT GAGGAGCTTG GCGGCGAGTG
5821 GGCCGACCGC TTCTTAGTCT TGTACGGCAT CGCAGCTCCC GACAGCCAGC GCATCGCCTT
5881 CTACCGCTTG CTCGACGAGT TCTTTTAATG ATCTAGAACC GGTCATGGCC GCAATAAAAT
5941 ATCTTTATTT TCATTACATC TGTGTGTTGG TTTTTTGTGT GCAATAAAAT AACTTCGTAT
6001 AGCATACATT ATACGAAGTT ATAGTAGTTT GCAAAGAAGC ATAAATGTTA TATATACTGC
6061 ATATATATAT GTATTTATTC AGGAATATAT ATTTTTCATT GGGAAAACTT TTCAACAGAA
6121 ATGGAGTGTA AAAGTTTTTC TTTGCGATAG AACTAAACAC ATGATTTCTT GATTAACAAA
6181 CCACTGCAGT AATAGAATAT GCAGAATGTC ATTTGACTAT AACAGATTTA TTTTGATTGC
6241 TGTGAGATAG TTTGTATATC TGAGTTATTA TTTTGATTAG TTGATACTTC CGTATTTAGT
6301 AACAGTTACA TAAAGGTTAC TGACCTGACA TATATTCTCA ATTGAACTAA CTACTGTATA
6361 GGAACTACAT GGAGGCCTAA AAGTTAGAAA AGTTTCTCT GACACATCAT GGATAAAATA
6421 AAGAATAAAA TGAGTTGGGA CGGATAATTG AAGGATGTGA AAAGTATTGA TAAAGATTTA
6481 ATTTTAATGT TTCTTACTCA CATTTACTAT TTCAAATGCT CTTTTCTGTA GCATATCATG
6541 ATAATTATTT CAAATAATGA TGTGATCTAT GCTATCAAAT GATCAGATGA TTTCTTGGGT
6601 AAACGACATA CAAACTTGAG GAACTCCTAA TTATATTTAG TAGTAAAGTC ACCTTGTTGT
6661 TTCATGTCTA TTATGAGCCA GCTTTTCAGT TCAATTTTTT AGTTTGTCTT TCATATAGAA
6721 ATACAACTAT TTCGTTTATT TTAAGAAAG TCATGATGAC TAATGAAGGA TTTAAAAATG
6781 GACTGTGGCA AACAGTAAAA ATAATATAT GATAAGGACT GTGTGTCCCG AAGAGATGGG
6841 AGTTTATCTC TAGAGGATCC GGGGATATCC TCGAGGTTCC CTTTAGTGAG GGTTAATTGC
6901 GAGCTTGGCG TAATCATGGT CATAGCTGTT TCCTGTGTGA AATTGTTATC CGCTCACAAT
6961 TCCACACAAC ATACGAGCCG GAAGCATAAA GTGTAAAGCC TGGGGTGCCT AATGAGTGAG
7021 CTAACTCACA TTAATTGCGT TGCGCTCACT GCCCGCTTTC CAGTCGGGAA ACCTGTCGTG
```

```
7081 CCAGCTGCAT TAATGAATCG GCCAACGCGC GGGGAGAGGC GGTTTGCGTA TTGGGCGCTC

7141 TTCCGCTTCC TCGCTCACTG ACTCGCTGCG CTCGGTCGTT CGGCTGCGGC GAGCGGTATC

7201 AGCTCACTCA AAGGCGGTAA TACGGTTATC CACAGAATCA GGGGATAACG CAGGAAAGAA

7261 CATGTGAGCA AAAGGCCAGC AAAAGGCCAG GAACCGTAAA AAGGCCGCGT TGCTGGCGTT

7321 TTTCCATAGG CTCCGCCCCC CTGACGAGCA TCACAAAAAT CGACGCTCAA GTCAGAGGTG

7381 GCGAAACCCG ACAGGACTAT AAAGATACCA GGCGTTTCCC CCTGGAAGCT CCCTCGTGCG

7441 CTCTCCTGTT CCGACCCTGC CGCTTACCGG ATACCTGTCC GCCTTTCTCC CTTCGGGAAG

7501 CGTGGCGCTT TCTCATAGCT CACGCTGTAG GTATCTCAGT TCGGTGTAGG TCGTTCGCTC

7561 CAAGCTGGGC TGTGTGCACG AACCCCCCGT TCAGCCCGAC CGCTGCGCCT TATCCGGTAA

7621 CTATCGTCTT GAGTCCAACC CGGTAAGACA CGACTTATCG CCACTGGCAG CAGCCACTGG

7681 TAACAGGATT AGCAGAGCGA GGTATGTAGG CGGTGCTACA GAGTTCTTGA AGTGGTGGCC

7741 TAACTACGGC TACACTAGAA GAACAGTATT TGGTATCTGC GCTCTGCTGA AGCCAGTTAC

7801 CTTCGGAAAA AGAGTTGGTA GCTCTTGATC CGGCAAACAA ACCACCGCTG GTAGCGGTGG

7861 TTTTTTTGTT TGCAAGCAGC AGATTACGCG CAGAAAAAAA GGATCTCAAG AAGATCCTTT

7921 GATCTTTTCT ACGGGGTCTG ACGCTCAGTG GAACGAAAAC TCACGTTAAG GGATTTTGGT

7981 CATGAGATTA TCAAAAAGGA TCTTCACCTA GATCCTTTTA AATTAAAAAT GAAGTTTTAA

8041 ATCAATCTAA AGTATATATG AGTAAACTTG GTCTGACAGT TACCAATGCT TAATCAGTGA

8101 GGCACCTATC TCAGCGATCT GTCTATTTCG TTCATCCATA GTTGCCTGAC TCCCCGTCGT

8161 GTAGATAACT ACGATACGGG AGGGCTTACC ATCTGGCCCC AGTGCTGCAA TGATACCGCG

8221 AGACCCACGC TCACCGGCTC CAGATTTATC AGCAATAAAC CAGCCAGCCG GAAGGGCCGA

8281 GCGCAGAAGT GGTCCTGCAA CTTTATCCGC CTCCATCCAG TCTATTAATT GTTGCCGGGA

8341 AGCTAGAGTA AGTAGTTCGC CAGTTAATAG TTTGCGCAAC GTTGTTGCCA TTGCTACAGG

8401 CATCGTGGTG TCACGCTCGT CGTTTGGTAT GGCTTCATTC AGCTCCGGTT CCCAACGATC

8461 AAGGCGAGTT ACATGATCCC CCATGTTGTG CAAAAAAGCG GTTAGCTCCT TCGGTCCTCC

8521 GATCGTTGTC AGAAGTAAGT TGGCCGCAGT GTTATCACTC ATGGTTATGG CAGCACTGCA

8581 TAATTCTCTT ACTGTCATGC CATCCGTAAG ATGCTTTTCT GTGACTGGTG AGTACTCAAC

8641 CAAGTCATTC TGAGAATAGT GTATGCGGCG ACCGAGTTGC TCTTGCCCGG CGTCAATACG

8701 GGATAATACC GCGCCACATA GCAGAACTTT AAAAGTGCTC ATCATTGGAA AACGTTCTTC

8761 GGGGCGAAAA CTCTCAAGGA TCTTACCGCT GTTGAGATCC AGTTCGATGT AACCCACTCG

8821 TGCACCCAAC TGATCTTCAG CATCTTTTAC TTTCACCAGC GTTTCTGGGT GAGCAAAAAC

8881 AGGAAGGCAA AATGCCGCAA AAAAGGGAAT AAGGGCGACA CGGAAATGTT GAATACTCAT

8941 ACTCTTCCTT TTTCAATATT ATTGAAGCAT TTATCAGGGT TATTGTCTCA TGAGCGGATA

9001 CATATTTGAA TGTATTTAGA AAAATAAACA AATAGGGGTT CCGCGCACAT TTCCCCGAAA

9061 AGTGCCAC
```

Complete Sequence of Human Micro-Dystrophin Vector, pE223-uH24hDys-dCT (SEQ ID NO: 22)

```
TTTCCTGCGTTATCCCCTGATTCTGTGGATAACCGTATTACCGCCTTTGAGTGAGCTGATACCGCTCGCCG
CAGCCGAACGACCGAGCGCAGCGAGTCAGTGAGCGAGGAAGCGGAAGAGCGCCCAATACGCAAACCGCCTC
TCCCCGCGCGTTGGCCGATTCATTAATGCAGCTGGCACGACAGGTTTCCCGACTGGAAAGCGGGCAGTGAG
CGCAACGCAATTAATACGCGTACCGCTAGCCAGGAAGAGTTTGTAGAAACGCAAAAAGGCCATCCGTCAGG
ATGGCCTTCTGCTTAGTTTGATGCCTGGCAGTTTATGGCGGGCGTCCTGCCCGCCACCCTCCGGGCCGTTG
CTTCACAACGTTCAAATCCGCTCCCGGCGGATTTGTCCTACTCAGGAGAGCGTTCACCGACAAACAACAGA
TAAAACGAAAGGCCCAGTCTTCCGACTGAGCCTTTCGTTTTATTTGATGCCTGGCAGTTCCCTACTCTCGC
GTTAACGCTAGCATGGATGTTTTCCCAGTCACGACGTTGTAAAACGACGGCCAGTCTTAAGCTCGGGCCCC
AAATAATGATTTTATTTTGACTGATAGTGACCTGTTCGTTGCAACAAATTGATGAGCAATGCTTTTTTATA
ATGCCAACTTTGTACAAAAAAGCAGGCTCAAGGGCCGTCAAGGCCCACCATGGACTACAAGGACGACGATG
ACAAGCTTTGGTGGGAAGAAGTAGAGGACTGTTATGAAAGAGAAGATGTTCAAAAGAAAACATTCACAAAA
TGGGTAAATGCACAATTTTCTAAGTTTGGGAAGCAGCATATTGAGAACCTCTTCAGTGACCTACAGGATGG
GAGGCGCCTCCTAGACCTCCTCGAAGGCCTGACAGGGCAAAAACTGCCAAAAGAAAAAGGATCCACAAGAG
TTCATGCCCTGAACAATGTCAACAAGGCACTGCGGGTTTTGCAGAACAATAATGTTGATTTAGTGAATATT
GGAAGTACTGACATCGTAGATGGAAATCATAAACTGACTCTTGGTTTGATTTGGAATATAATCCTCCACTG
GCAGGTCAAAAATGTAATGAAAAATATCATGGCTGGATTGCAACAAACCAACAGTGAAAAGATTCTCCTGA
GCTGGGTCCGACAATCAACTCGTAATTATCCACAGGTTAATGTAATCAACTTCACCACCAGCTGGTCTGAT
GGCCTGGCTTTGAATGCTCTCATCCATAGTCATAGGCCAGACTTATTTGACTGGAATAGTGTGGTTTGCCA
GCAGTCAGCCACACAACGACTGGAACATGCATTCAACATCGCCAGATATCAATTAGGCATAGAGAAACTAC
TCGATCCTGAAGATGTTGATACCACCTATCCAGATAAGAAGTCCATCTTAATGTACATCACATCACTCTTC
CAAGTTTTGCCTCAACAAGTGAGCATTGAAGCCATCCAGGAAGTGGAAATGTTGCCAAGGCCACCTAAAGT
GACTAAAGAAGAACATTTTCAGTTACATCATCAAATGCACTATTCTCAACAGATCACGGTCAGTCTAGCAC
AGGGATATGAGAGAACTTCTTCCCCTAAGCCTCGATTCAAGAGCTATGCCTACACACAGGCTGCTTATGTC
ACCACCTCTGACCCTACACGGAGCCCATTTCCTTCACAGCATTTGGAAGCTCCTGAAGACAAGTCATTTGG
CAGTTCATTGATGGAGAGTGAAGTAAACCTGGACCGTTATCAAACAGCTTTAGAAGAAGTATATCGTGGC
TTCTTTCTGCTGAGGACACATTGCAAGCACAAGGAGAGATTTCTAATGATGTGGAAGTGGTGAAAGACCAG
TTTCATACTCATGAGGGGTACATGATGGATTTGACAGCCCATCAGGGCCGGGTTGGTAATATTCTACAATT
GGGAAGTAAGCTGATTGGAACAGGAAAATTATCAGAAGATGAAGAAACTGAAGTACAAGAGCAGATGAATC
TCCTAAATTCAAGATGGGAATGCCTCAGGGTAGCTAGCATGGAAAAACAAAGCAATTTACATAGAGTTTTA
ATGGATCTCCAGAATCAGAAACTGAAAGAGTTGAATGACTGGCTAACAAAAACAGAAGAAAGAACAAGGAA
AATGGAGGAAGAGCCTCTTGGACCTGATCTTGAAGACCTAAAACGCCAAGTACAACAACATAAGGTGCTTC
AAGAAGATCTAGAACAAGAACAAGTCAGGGTCAATTCTCTCACTCACATGGTGGTGGTAGTTGATGAATCT
AGTGGAGATCACGCAACTGCTGCTTTGGAAGAACAACTTAAGGTATTGGGAGATCGATGGGCAAACATCTG
TAGATGGACAGAAGACCGCTGGGTTCTTTTACAAGACATCCTTCTCAAATGGCAACGTCTTACTGAAGAAC
AGTGCCTTTTTAGTGCATGGCTTTCAGAAAAAGAAGATGCAGTGAACAAGATTCACACAACTGGCTTTAAA
GATCAAAATGAAATGTTATCAAGTCTTCAAAAACTGGCCGTTTTAAAAGCGGATCTAGAAAAAGAAAAAGCA
ATCCATGGGCAAACTGTATTCACTCAAACAAGATCTTCTTTCAACACTGAAGAATAAGTCAGTGACCCAGA
AGACGGAAGCATGGCTGGATAACTTTGCCCGGTGTTGGGATAATTTAGTCCAAAAACTTGAAAAGAGTACA
GCACAGATTTCACAGGCTGTCACCACCACTCAGCCATCACTAACACAGACAACATGTAATGAAACAGTAAC
TACGGTGACCACAAGGGAACAGATCCTGGTAAAGCATGCTCAAGAGGAACTTCCACCACCACCTCCCCAAA
AGAAGAGGCAGATTACTGTGGATCTTGAAAGACTCCAGGAACTTCAAGAGGCCACGGATGAGCTGGACCTC
AAGCTGCGCCAAGCTGAGGTGATCAAGGGATCCTGGCAGCCCGTGGGCGATCTCCTCATTGACTCTCTCCA
AGATCACCTCGAGAAAGTCAAGGCACTTCGAGGAGAAATTGCGCCTCTGAAAGAGAACGTGAGCCACGTCA
ATGACCTTGCTCGCCAGCTTACCACTTTGGGCATTCAGCTCTCACCGTATAACCTCAGCACTCTGGAAGAC
CTGAACACCAGATGGAAGCTTCTGCAGGTGGCCGTCGAGGACCGAGTCAGGCAGCTGCATGAAGCCCACAG
GGACTTTGGTCCAGCATCTCAGCACTTTCTTTCCACGTCTGTCCAGGGTCCCTGGGAGAGAGCCATCTCGC
CAAACAAAGTGCCCTACTATATCAACCACGAGACTCAAACAACTTGCTGGGACCATCCCAAAATGACAGAG
CTCTACCAGTCTTTAGCTGACCTGAATAATGTCAGATTCTCAGCTTATAGGACTGCCATGAAACTCCGAAG
ACTGCAGAAGGCCCTTTGCTTGGATCTCTTGAGCCTGTCAGCTGCATGTGATGCCTTGGACCAGCACAACC
TCAAGCAAATGACCAGCCCATGGATATCCTGCAGATTATTAATTGTTTGACCACTATTTATGACCGCCTG
GAGCAAGAGCACAACATTTGGTCAACGTCCCTCTCTGCGTGGATATGTGTCGAACTGGCTGCTGAATGT
TTATGATACGGACGAACAGGGAGGATCCGTGTCCTGTCTTTTAAAACTGGCATCATTTCCCTGTGTAAAG
CACATTTGGAAGACAAGTACAGATACCTTTCAAGCAAGTGGCAAGTTCAACAGGATTTTGTGACCAGCGC
AGGCTGGGCCTCCTTCTGCATGATTCTATCCAAATTCCAAGACAGTTGGGTGAAGTTGCATCCTTTGGGGG
CAGTAACATTGAGCCAAGTGTCCGGAGCTGCTTCCAATTTGCTAATAATAAGCCAGAGATCGAAGCGGCCC
TCTTCCTAGACTGGATGAGACTGGAACCCCAGTCCATGGTGGCTGCCGTCCGTCTGCACAGATGGCTGCT
GCAGAAACTGCCAAGCATCAGGCCAAATGTAACATCTGCAAAGAGTGTCCAATCATTGGATTCAGGTACAG
GAGTCTAAAGCACTTTAATTATGACATCTGCCAAAGCTGCTTTTTTTCTGGTCGAGTTGCAAAAGGCCATA
AAATGCACTATCCCATGGTGGAATATTGCACTCCGACTACATCAGGAGAAGATGTTCGAGACTTTGCCAAG
GTACTAAAAAACAAATTTCGAACCAAAAGGTATTTTGCAAAGCATCCCCGAATGGGCTACCTGCCAGTGCA
GACTGTCTTAGAGGGGGACAACATGGAAACTGACACAATGTGACTCATGGGCCGACCCAGCTTTCTTGTAC
AAAGTTGGCATTATAAGAAAGCATTGCTTATCAATTTGTTGCAACGAACAGGTCACTATCAGTCAAAATAA
AATCATTATTTGCCATCCAGCTGATATCCCCTATAGTGAGTCGTATTACATGGTCATAGCTGTTTCCTGGC
AGCTCTGGCCCGTGTCTCAAAATCTCTGATGTTACATTGCACAAGATAAAAATATATCATCATGCCTCCTC
TAGACCAGCCAGGACAGAAATGCCTCGACTTCGCTGCTACCCAAGGTTGCCGGGTGACGCACACCGTGGAA
ACGGATGAAGGCACGAACCCAGTGGACATAAGCCTGTTCGGTTCGTAAGCTGTAATGCAAGTAGCGTATGC
GCTCACGCAACTGGTCCAGAACCTTGACCGAACGCAGCGGTGGTAACGGCGCAGTGGCGGTTTTCATGGCT
TGTTATGACTGTTTTTTTGGGGTACAGTCTATGCCTCGGGCATCCAAGCAGCAAGCGCGTTACGCCGTGGG
TCGATGTTTGATGTTATGGAGCAGCAACGATGTTACGCAGCAGGGCAGTCGCCCTAAAACAAAGTTAAACA
TCATGAGGGAAGCGGTGATCGCCGAAGTATCGACTCAACTATCAGAGGTAGTTGGCGTCATCGAGCGCCAT
CTCGAACCGACGTTGCTGGCCGTACATTTGTACGGCTCCGCAGTGGATGGCGGCCTGAAGCCACACAGTGA
TATTGATTTGCTGGTTACGGTGACCGTAAGGCTTGATGAAACAACGCGGCGAGCTTTGATCAACGACCTTT
TGGAAACTTCGGCTTCCCCTGGAGAGAGCGAGATTCTCCGCGCTGTAGAAGTCACCATTGTTGTGCACGAC
GACATCATTCCGTGGCGTTATCCAGCTAAGCGCGAACTGCAATTTGGAGAATGGCAGCGCAATGACATTCT
TGCAGGTATCTTCGAGCCAGCCACGATCGACATTGATCTGGCTATCTTGCTGACAAAAGCAAGAGAACATA
GCGTTGCCTTGGTAGGTCCAGCGGCGGAGGAACTCTTTGATCCGGTTCCTGAACAGGATCTATTTGAGGCG
CTAAATGAAACCTTAACGCTATGGAACTCGCCGCCCGACTGGGCTGGCGATGAGCGAAATGTAGTGCTTAC
```

-continued

```
GTTGTCCCGCATTTGGTACAGCGCAGTAACCGGCAAAATCGCGCCGAAGGATGTCGCTGCCGACTGGGCAA
TGGAGCGCCTGCCGGCCCAGTATCAGCCCGTCATACTTGAAGCTAGACAGGCTTATCTTGGACAAGAAGAA
GATCGCTTGGCCTCGCGCGCAGATCAGTTGGAAGAATTTGTCCACTACGTGAAAGGCGAGATCACCAAGGT
AGTCGGCAAATAACCCTCGAGCCACCCATGACCAAAATCCCTTAACGTGAGTTACGCGTCGTTCCACTGAG
CGTCAGACCCCGTAGAAAAGATCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGAGCTACCAACTCTTTTTCCGAA
GGTAACTGGCTTCAGCAGAGCGCAGATACCAAATACTGTCCTTCTAGTGTAGCCGTAGTTAGGCCACCACT
TCAAGAACTCTGTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGGTCGGGCTGAAC
GGGGGGTTCGTGCACACAGCCCAGCTTGGAGCGAACGACCTACACCGAACTGAGATACCTACAGCGTGAGC
ATTGAGAAAGCGCCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGGGTTCGCCACCT
CTGACTTGAGCGTCGATTTTTGTGATGCTCGTCAGGGGGCGGAGCCTATGGAAAAACGCCAGCAACGCGG
CCTTTTTACGGTTCCTGGCCTTTTGCTGGCCTTTTGCTCACATGTT
```

Left Arm PCR (830 bp) Sequence, Primers are in Bold:

(SEQ ID NO: 23)
```
AGCAGGAAAACATGTCCCATGAGACCTATACACACACATTCTGCCTTCAGAATTCAGCTGCTGCATTCTG
CTGCTGCTTCTCTTATTCAGACTGTTGGCATCATCAATACATAACTTTTGATTGAATCCCAAGGGGAAAAA
TAACTTTGGTAGACAGTGGATACATAACAAATGCATGGATTATTCTGGGCATTCCTTTTTATTTGGTAGAGT
GAAATTTTTGGTGTTGTTGAGAGGATAAAAAAGGCATTTAAAAGTCAATTTTGAATCCGGATTTTCTGCTCT
GTTAATAAATTCACATGAAAGTTACAGAAAGTATTGTTATGCTTTTGTACTGAATAGTTTTTGTGTTTAGAA
GGCTTTAAAAGCAAGTACTATGTCCACTGTGCTATTCTGGTTTGGATATTAATCAGAACACAGTTGAGCATT
GTTTGAATTCACAGAGCTTGCCATGCTGGAAGCACAACCTTATATGTAGTGACCATGGACAGTCCTATTATG
GGAAACCAACTTGAGAGAGAAGGCGGGTCACTTGCTTGTGCGCAGGTCCTGGAATTTGAAATATCCGGGGGC
CTCTACAGAATCCTGGCATCAGTTACTGTGTTGACTCACTCAGTGTTGGGATCACTCACTTTCCCCCTACAG
GACTCAGATCTGGGAGGCAATTACCTTCGGAGAAAAACGAATAGGAAAAACTGAAGTGTTACTTTTTTTAAA
GCTGCTGAAGTTTGTTGGTTTCTCATTGTTTTTAAGCCTACTGGAGCAATAAAGTTTGAAGAACTTTTACCA
GGTTTTTTTTATCGCTGCCTTGATATACACTTTTCAAA
```

(SEQ ID NO: 24)
```
AGTAGTTTGCAAAGAAGCATAAATGTTATATATACTGCATATATATATGTATTTATTCAGGAATATATATTT
TTCATTGGGAAAACTTTTCAACAGAAATGGAGTGTAAAAGTTTTTCTTTGCGATAGAACTAAACACATGATT
TCTTGATTAACAAACCACTGCAGTAATAGAATATGCAGAATGTCATTTGACTATAACAGATTTATTTTGATT
GCTGTGAGATAGTTTGTATATCTGAGTTATTATTTTGATTAGTTGATACTTCCGTATTTAGTAACAGTTACA
TAAAGGTTACTGACCTGACATATATTCTCAATTGAACTAACTACTGTATAGGAACTACATGGAGGCCTAAAA
GTTAGAAAAAGTTTCTCTGACACATCATGGATAAAATAAAGAATAAAATGAGTTGGGACGGATAATTGAAGG
ATGTGAAAGTATTGATAAAGATTTAATTTTAATGTTTCTTACTCACATTTACTATTTCAAATGCTCTTTTC
TGTAGCATATCATGATAATTATTTCAAATAATGATGTGATCTATGCTATCAAATGATCAGATGATTTCTTGG
GTAAACGACATACAAACTTGAGGAACTCCTAATTATATTTAGTAGTAAAGTCACCTTGTTGTTTCATGTCTA
TTATGAGCCAGCTTTTCAGTTCAATTTTTTAGTTTGTCTTTCATATAGAAATACAACTATTTCGTTTATTTT
TAAGAAAGTCATGATGACTAATGAAGGATTTAAAAATGGACTGTGGCACAACAGTAAAAATAATATATGATA
AGGACTGTGTGTCCCGAAGAGATGGGAGTTTATCTC
```

Right Arm PCR (828 bp) Sequence, Primers in Bold: DMD Locus
Dystrophin atg=bold lowercase, TALEN recognition site=underlined, (TALEN cutting site)

In bold italics—the Homology arms

TALEN:40 id the first one that bind the ATG
TALEN 52 is the second one (Cooper Black Font)

(SEQ ID NO: 25)
```
GCCCCAAAACAATTTTTTCATTTTTTCTATGTTGTTTTATGAAAATTTTGCTTATATGCATATTTAGACAAC

CACACTGAGAGGAAAGGAGGTGACCTAGGGAAAAGAATGTTTAAATTAAAATTAGGCCTTATGTTTTATCT

CATACACCTTTTGCTGGGAAAATAGCAATGTTATGACAATAATATTCTAAAACACAAAATGTACAATTAAC

TATTAAGGTAAACATCACAGTCTGACTCAATATTTTTTAATTTTATCTATTACTCATTGCAGTCGCAAGC

AGTTGAATGTTTGACATAGAAAATGAGTCTGTCACTTTAACAAATGGTACAATAAAAACACTCAAACAAAA

ATTTTAGTAGGGATTATTATAACTATAAAAAGAATATCTTTCTTTAAAAAATGTTTCCAATGTTTTCTATCA

ATTTTGGGCTCGCCTGTTGCATAAAAGTAATAAGGAACAAGATGAAGAAGCTTTCTATTGGCAAAGAATGAT

TTACATGCTGAATGACATAATACAACTGTATTCACTTAATACAGAAAACAAGCCTCTATTCAGAACCATTAA

ATGATCATTAACTCAATGTCTAAAAAAATGGTGTTTTAAGAATTGGCACCAGAGAAATGGAAGAAAGAATAA

TTTGTTAGTAAAGAAGTTTTAGCATAATTCACAACTGAAATTTAGGATTTGAGAAAAATTTCTTTCCTGCAT

TATAAGAGTATTCTTTATTTT*AGCAGGAAAACATGTCCCATGAGACCTATACACACACATTCTGCCTTCA*

*GAATTCAGCTGCTGCATTCTGCTGCTGCTTCTCTTATTCAGACTGTTGGCATCATCAATACATAACTTTTGA*

*TTGAATCCCAAGGGGAAAAAATAACTTTGGTAGACAGTGGATACATAACAAATGCATGGATTATTCTGGGCA*
```

```
TTCCTTTTTATTTGGTAGAGTGAAATTTTTGGTGTTGTTGAGAGGATAAAAAAGGCATTTAAAAGTCAATTT
TGAATCCGGATTTTCTGCTCTGTTAATAAATTCACATGAAAGTTACAGAAAGTATTGTTATGCTTTTGTACT
GAATAGTTTTTGTGTTTAGAAGGCTTTAAAAGCAAGTACTATGTCCACTGTGCTATTCTGGTTTGGATATTA
ATCAGAACACAGTTGAGCATTGTTTGAATTCACAGAGCTTGCCATGCTGGAAGCACAACCTTATATGTAGTG
ACCATGGACAGTCCTATTATGGGAAACCAACTTGAGAGAGAAGGCGGGTCACTTGCTTGTGCGCAGGTCCTG
GAATTTGAAATATCCGGGGGCCTCTACAGAATCCTGGCATCAGTTACTGTGTTGACTCACTCAGTGTTGGGA
TCACTCACTTTCCCCCTACAGGACTCAGATCTGGGAGGCAATTACCTTCGGAGAAAAACGAATAGGAAAAA
TGAAGTGTTACTTTTTTTAAAGCTGCTGAAGTTTGTTGGTTTCTCATTGTTTTTAAGCCTACTGGAGCAATA
AAGTTTGAAGAACTTTTACCAGGTTTTTTTATCGCTGCCTTGATATACACTTTTCAAAatgCTT(TGGTGG
GAAGAAGT)AGAGGACTGTTGTAAGTACAAAGTAACTAAAAATATATTTTACTGTGGCATAACGT(T
TAGTTTGTGACAAGCTCACT)AATTAGGTAGATTGATTTTAAATTATCACAGTAGTTTGCAAAG
AAGCATAAATGTTATATATACTGCATATATATGTATTTATTCAGGAATATATATTTTTCATTGGGAAAAC
TTTTCAACAGAAATGGAGTGTAAAAGTTTTTCTTTGCGATAGAACTAAACACATGATTTCTTGATTAACAAA
CCACTGCAGTAATAGAATATGCAGAATGTCATTTGACTATAACAGATTTATTTTGATTGCTGTGAGATAGTT
TGTATATCTGAGTTATTATTTTGATTAGTTGATACTTCCGTATTTAGTAACAGTTACATAAAGGTTACTGAC
CTGACATATATTCTCAATTGAACTAACTACTGTATAGGAACTACATGGAGGCCTAAAAGTTAGAAAAAGTTT
CTCTGACACATCATGGATAAAATAAAGAATAAAATGAGTTGGGACGGATAATTGAAGGATGTGAAAAGTATT
GATAAAGATTTAATTTTAATGTTTCTTACTCACATTTACTATTTCAAATGCTCTTTTCTGTAGCATATCATG
ATAATTATTTCAAATAATGATGTGATCTATGCTATCAAATGATCAGATGATTTCTTGGGTAAACGACATACA
AACTTGAGGAACTCCTAATTATATTTAGTAGTAAAGTCACCTTGTTGTTTCATGTCTATTATGAGCCAGCTT
TTCAGTTCAATTTTTAGTTTGTCTTTCATATAGAAATACAACTATTTCGTTTATTTTTAAGAAAGTCATGA
TGACTAATGAAGGATTTAAAAATGGACTGTGGCACAACAGTAAAAATAATATATGATAAGGACTGTGTGTCC
CGAAGAGATGGGAGTTTATCTCTTCCCCACCCATCTTTGACTTGTGGAGTGTAGTTATTCTAAAATAGATAT
GAGGGCAATGCCTATAATTAAGAATGAAAAATAAATCTCTCCAAATAAGTAATGCTCCACAACTACTAAAA
AAAAAGGCAGAAGTTTTGCCACTGGGAAAACTTTGTGGAAATAAGTTAACATTGTCCATGTATTGAGTCACA
TTAAAAGCTACCAGACTTTATAATACAATATTTACTTACATTGTTGGCTTGCTTCATAAATTTCTTTTGGTG
GACATCATTATTACTTTTAGATTGAAAACTATTATATTTACTATCATTACAAATATATGCATGGCATATAT
CTGTTGTTTGCAATATACACACATTTTTATTTTTGTTTTTATTTCTTTGATATATGTAACATAAATACC
ATCAAAATCACTAGTGATTTTATATATATATATATTCTACATAATTAACATCATATACAAGTATATAGAGCA
ATTTTGAAAGAATATATGCAATTCTGCTGAAATTAAGCAAGGTAAATCTACACTCTGCTTTGTCATAGATAT
TCAAATAACTTTCAATTCTTAGAATGCGAAGAAAGGTAATCTTTTTGGGACATGCCCTGTAGGATTTTTCA
CGCTGCATTTAAAAAATCATCAAGTAATGCCTATGCAACATGACAATGAGTTTGGTAAGAAAAAACGGAGAT
ATACTCAGGGCTATATTATACATTAAATTTTGCTGTTTGACAACATACTGCTACTTGGATGTTTGACATTTG
AATCCAGTTTGTAAATTTGCCGTAGTTTGATAAACTTACAAAAGTACGTTTTGTTGTTTTTTAACCAAAACA
GTTACCCTTTAAAAGAGATCACTGTATTGTCAAACATATTGTATTGTTCACTTTTAGAATTACTCAAATAAT
GCATTGTAAAGAATTATTCAAATAGTGTACTGCAAATAGACATTTCATTTGAATATATTTAAATGATGTAAG
TCATCTGAGGTCTAATAAAAATCACCTTTTAGAATTTCATCTGCAGAATCTTTTAAAGACATCTTAACTACGA
AAAAGAGATTGCTGATCTAAATTGATGATATACTGTTAATACAAAGCTTTTGGTGTATCTTACATGACATAAA
CATTATGAAAAATACAATAGAGTATGTCATATAGATGTTACTCTAAACTTTAAAAAAAGACTACAAAGTGTT
```

-continued

```
CTATGCATAATTACATTATTTAAGGGGAAAAAGGTGTTGGCTGACACTATTCCAGCTAGACAGTACTGAATT

GCAAATTCATCATTTGGGCACAGATATTAATACAGCTTCCTCTTTATTCCTATAGCATTCATTTGAAATCCC

TGTACTCCATGTCATTTGCTACATATGAAACAAATTGTCAAGTTTTTAACCACTTGTGTAGTTTAATAAAAG

AGATTAAAATCATTGTCTTGGAAACATCAGGTGTTTTTCAAAATTCTATTTTATTATCTTTCATCAAAATTT

TATCTCAAGA
```

Homologous Recombination Vector
(MC1 PROMOTER AND HSVTK; (UNDERLINED SEQUENCE)) REF.: WEB.NCIFCRF.GOV/RESEARCH/BRB/PRODUCTDATASHEETS/RECOMBINEERING/PLASMID/PL253_ANNOTATED.TXT
POLYA: SV40 (UNDERLINED AND BOLD) REF. NCBI.NLM.NIH.GOV/NUCCORE/DQ188838
5' ARM REF. DYSTROPHYN SEQUENCE.
CHIM_INT (ITALICS): LABLIFE.ORG/G?A=SEQA&ID=VDB_G2.RNXYZ5XL NOT9LRBMUCEEJBP VPHE-_SEQUENCE_D795A0E123E1BDF1976B FC35D4BE87AB216D9B7_10#
XHOI/NOTI SEQUENCES
POLYA: SV40 (UNDERLINED AND BOLD) REF. NCBI.NLM.NIH.GOV/NUCCORE/DQ188838
LOXP REF.: TARGETED INTEGRATION OF DNA USING MUTANT LOX SITES IN EMBRYONIC STEM CELLS
HEF1-ELF4G PROM. PORF CVS PLASMID (lower case underlined)
EGFP( ) PSAM2 PLASMID
2A SEQUENCE (lowercase italics)
NEO+SINTETIC POLYA (lowercase, underlined, bold) PGL4.18 (PGL4.18 was purchased from Promega); promega.com/~/media/Files/Resources/Protocols/Product %20Information %2Sheets/A/pGL418%20Vector.pdf)
LOXP REF.: TARGETED INTEGRATION OF DNA USING MUTANT LOX SITES IN EMBRYONIC STEM CELLS
3'ARM (lower case) REF.: DYSTROPHYN SEQUENCE (SEQ ID NO: 26)
```
TCTAGAGTCGAGCAGTGTGGTTTTCAAGAGGAAGCAAAAAGCCTCTCCACCCAGGCCTGGAATGTTTCCACCCAATG

TCGAGCAGTGTGGTTTTGCAAGAGGAAGCAAAAAGCCTCTCCACCCAGGCCTGGAATGTTTCCACCCAATGTCGAGC

AAACCCCGCCCAGCGTCTTGTCATTGGCGAATTCGAACACGCAGATGCAGTCGGGGCGGCGCGGTCCCAGGTCCACT

TCGCATATTAAGGTGACGCGTGTGGCCTCGAACACCGAGCGACCCTGCAGCGACCCGCTTAACAGCGTCAACAGCGT

GCCGCAGATCTTGGTGGCGTGAAACTCCCGCACCTCTTCGGCCAGCGCCTTGTAGAAGCGCGTATGGCTTCGTACCC

CGGCCATCAGCACGCGTCTGCGTTCGACCAGGCTGCGCGTTCTCGCGGCCATAGCAACCGACGTACGGCGTTGCGCC

CTCGCCGGCAGCAAGAAGCCACGGAAGTCCGCCCGGAGCAGAAAATGCCCACGCTACTGCGGGTTTATATAGACGGT

CCCCACGGGATGGGGAAAACCACCACCACGCAACTGCTGGTGGCCCTGGGTTCGCGCGACGATATCGTCTACGTACC

CGAGCCGATGACTTACTGGCGGGTGCTGGGGGCTTCCGAGACAATCGCGAACATCTACACCACACAACACCGCCTTG

ACCAGGGTGAGATATCGGCCGGGGACGCGGCGGTGGTAATGACAAGCGCCCAGATAACAATGGGCATGCCTTATGCC

GTGACCGACGCCGTTCTGGCTCCTCATATCGGGGGGGAGGCTGGGAGCTCACATGCCCCGCCCCCGGCCCTCACCCT

CATCTTCGACCGCCATCCCATCGCCGCCCTCCTGTGCTACCCGGCCGCGCGATACCTTATGGGCAGCATGACCCCCC

AGGCCGTGCTGGCGTTCGTGGCCCTCATCCCGCCGACCTTGCCCGGCACAAACATCGTGTTGGGGGCCCTTCCGGAG

GACAGACACATCGACCGCCTGGCCAAACGCCAGCGCCCCGGCGAGCGGCTTGACCTGGCTATGCTGGCCGCGATTCG

CCGCGTTTACGGGCTGCTTGCCAATACGGTGCGGTATCTGCAGGGCGGCGGGTCGTGGCGGGAGGATTGGGGACAGC

TTTCGGGGACGGCCGTGCCGCCCCAGGGTGCCGAGCCCCAGAGCAACGCGGGCCCACGACCCCATATCGGGGACACG

TTATTTACCCTGTTTCGGGCCCCCGAGTTGCTGGCCCCCAACGGCGACCTGTACAACGTGTTTGCCTGGGCCTTGGA

CGTCTTGGCCAAACGCCTCCGTCCCATGCACGTCTTTATCCTGGATTACGACCAATCGCCCGCCGGCTGCCGGGACG

CCCTGCTGCAACTTACCTCCGGGATGATCCAGACCCACGTCACCACCCCAGGCTCCATACCGACGATCTGCGACCTG

GCGCGCACGTTTGCCCGGGAGATGGGGGAGGCTAACTGAAACACGGAAGGAGACAATACCGAAGGAACCCGCGCTA

TGACGGCAATAAAAAGACAGAACAGACATGATAAGATACATTGATGAGTTTGGACAAACCACAACTAGAATGCAGTG

AAAAAAATGCTTTATTTGTGAAATTTGTGATGCTATTGCTTTATTTGTGAAATTTGTGATGCTATTGCTTTATTTGT
```

AACCATTATAAGCTGCAATAAACAAGTTAACAACAACAATTGCATTCATTTTATGTTTCAGGTTCAGGGGGAGGTGT

GGGAGGTTTTTTAAAGCAAGTAAAACCTCTACAAATGTGGTAGATCCATTTAAATGTTAATTAAagcaggaaaacat gtcccatgagacctatacacacacattctgccttcagaattcagctgctgcattctgctgctgcttctcttattc agactgttggcatcatcaatacataacttttgattgaatcccaaggggaaaaaataactttggtagacagtggatac ataacaaatgcatggattattctgggcattccttttatttggtagagtgaaattttggtgttgttgagaggataa aaaaggcatttaaaagtcaattttgaatccggattttctgctctgttaataaattcacatgaaagttacagaaagta ttgttatgcttttgtactgaatagttttgtgtttagaaggctttaaaagcaagtactatgtccactgtgctattct ggtttggatattaatcagaacacagttgagcattgtttgaattcacagagcttgccatgctggaagcacaaccttat atgtagtgaccatggacagtcctattatgggaaaccaacttgagagagaaggcgggtcacttgcttgtgcgcaggtc ctggaatttgaaatatccgggggcctctacagaatcctggcatcagttactgtgttgactcactcagtgttgggatc actcactttccccctacaggactcagatctgggaggcaattaccttcggagaaaaacgaataggaaaaactgaagtg ttacttttttaaagctgctgaagtttgttggtttctcattgtttttaagcctactggagcaataaagtttgaagaa cttttaccaggttttttttatcgctgccttgatatacacttttcaaaGTAAGTATCAAGGTTACAAGACAGGTTTAA

GGAGACCAATAGAAACTGGGCTTGTCGAGACAGAGAAGACTCTTGCGTTTCTGATAGGCACCTATTGGTCTTACTGA

CATCCACTTTGCCTTTCTCTCCACAGCTCGAGTCGCGGCCGCCAGACATGATAAGATACATTGATGAGTTTGGACAA

ACCACAACTAGAATGCAGTGAAAAAAATGCTTTATTTGTGAAATTTGTGATGCTATTGCTTTATTTGTGAAATTTGT

GATGCTATTGCTTTATTTGTAACCATTATAAGCTGCAATAAACAAGTTAACAACAACAATTGCATTCATTTTATGTT

TCAGGTTCAGGGGGAGGTGTGGGAGGTTTTTTAAAGCAAGTAAAACCTCTACAAATGTGGTAGATCCATTTAAATGT

TAATTAAATAACTTCGTATAGCATACATTATACGAAGTTATggatctgcgatcgctccggtgcccgtcagtgggcag agcgcacatcgcccacagtccccgagaagttgggggagggtcggcaattgaaccggtgcctagagaaggtggcgc ggggtaaactgggaaagtgatgtcgtgtactggctccgccttttttcccgagggtgggggagaaccgtatataagtgc agtagtcgccgtgaacgttctttttcgcaacgggtttgccgccagaacacagctggtgggtagggatgagggagggga ggggcattgtgatgtacagggctgctctgtgagatcaaggggtctcttaagggtgggagctggggcagggactacgag agcagccagatgggctgaaagtggaactcaagggggtttctggcacctacctacctgcttcccgctgggggtgggga gttggcccagagtcttaagattggggcagggtggagaggtgggctcttcctgcttcccactcatcttatagctttct ttccccagatccgaattcgagatccaaaccaaggaggaaaggatatcacagaggagaATGGTGAGCAAGGGCGAGGA

GCTGTTCACCGGGGTGGTGCCCATCCTGGTCGAGCTGGACGGCGACGTAAACGGCCACAAGTTCAGCGTGTCTGGCG

AGGGCGAGGGCGATGCCACCTACGGCAAGCTGACCCTGAAGTTCATCTGCACCACCGGCAAGCTGCCCGTGCCCTGG

CCCACCCTCGTGACCACCCTGACCTACGGCGTGCAGTGCTTCAGCCGCTACCCCGACCACATGAAGCAGCACGACTT

CTTCAAGTCCGCCATGCCCGAAGGCTACGTCCAGGAGCGCACCATCTTCTTCAAGGACGACGGCAACTACAAGACCC

GCGCCGAGGTGAAGTTCGAGGGCGACACCCTGGTGAACCGCATCGAGCTGAAGGGCATCGACTTCAAGGAGGACGGC

AACATCCTGGGGCACAAGCTGGAGTACAACTACAACAGCCACAACGTCTATATCATGGCCGACAAGCAGAAGAACGG

CATCAAGGCGAACTTCAAGATCCGCCACAACATCGAGGACGGCAGCGTGCAGCTCGCCGACCACTACCAGCAGAACA

CCCCCATCGGCGACGGCCCCGTGCTGCTGCCCGACAACCACTACCTGAGCACCCAGTCCGCCCTGAGCAAAGACCCC

AACGAGAAGCGCGATCACATGGTCCTGCTGGAGTTCGTGACCGCCGCCGGGATCACTCTCGGCATGGACGAGCTGTA

CAAGTAAagagccgagggcaggggaagtcttctaacatgcggggacgtggaggaaaatcccgggcccatcgaacaag acggcctccatgctggcagtcccgcagcttgggtcgaacgcttgttcgggtacgactgggcccagcagaccatcgga tgtagcgatgcggccgtgttccgtctaagcgctcaaggccggccctgctgttcgtgaagaccgacctgagcggcgc cctgaacgagcttcaagacgaggctgcccgcctgagctggctggccaccaccggcgtaccctgcgccgctgtgttgg atgttgtgaccgaagccggccgggactggctgctgctgggcgaggtccctggccaggatctgctgagcagccacctt gccccgctgagaaggtttctatcatggccgatgcaatgcggcgcctgcacaccctggacccgctacctgcccctt cgaccaccaggctaagcatcggatcgagcgtgctcggacccgcatggaggccggcctggtggaccaggacgacctgg acgaggagcatcagggcctggcccccgctgaactgttcgcccgactgaaagcccgcatgccggacggtgaggacctg gttgtcacacacggagatgcctgcctccctaacatcatggtcgagaatggccgcttctccggcttcatcgactgcgg tcgcctaggagttgccgaccgctaccaggacatcgccctggccaccgcgacatcgctgaggagcttggcggcgagt gggccgaccgcttcttagtcttgtacggcatcgcagctcccgacagccagcgcatcgccttctaccgcttgctcgac gagttcttttaatgatctagaaccggtcatggccgcaataaaatatctttattttcattacatctgtgtgttggttt tttgtgtgagtagtttgcaaagaagcataaatgttatatatactgcatatatatatgtatttattcaggaatatata tttttcattgggaaaacttttcaacagaaatggagtgtaaaagttttctttgcgatagaactaaacacatgatttc ttgattaacaaaccactgcagtaatagaatatgcagaatgtcatttgactataacagatttattttgattgctgtga gatagtttgtatatctgagttattattttgattagttgatacttccgtatttagtaacagttacataaaggttactg acctgacatatattctcaattgaactaactactgtataggaactacatggaggcctaaaagttagaaaaagtttctc tgacacatcatggataaaataaagaataaaatgagttgggacggataattgaaggatgtgaaaagtattgataaaga tttaattttaatgtttcttactcacatttactatttcaaatgctcttttctgtagcatatcatgataattatttcaa ataatgatgtgatctatgctatcaaatgatcagatgatttcttgggtaaacgacatacaaacttgaggaactcctaa ttatatttagtagtaaagtcaccttgttgtttcatgtctattatgagccagcttttcagttcaatttttttagtttgt ctttcatatagaaatacaactatttcgtttatttttaagaaagtcatgatgactaatgaaggatttaaaaatggact gtggcacaacagtaaaaataatatatgataaggactgtgtgtcccgaagagatgggagtttatctc Example 2

Figure 3:
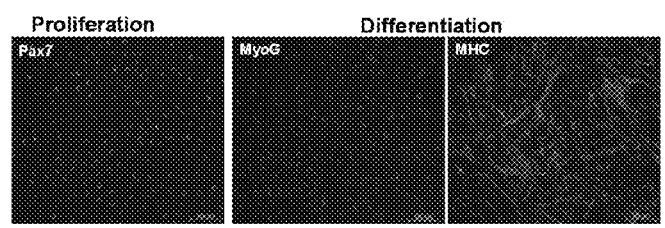
FIG. 3 demonstrates myogenic differentiation of DMD iPS cells. Pax7 is expressed in proliferating modified myogenic progenitors and corresponding myotubes express Myogenin (MyoG) and myosin-heavy-chain MHC.
Figure 4:
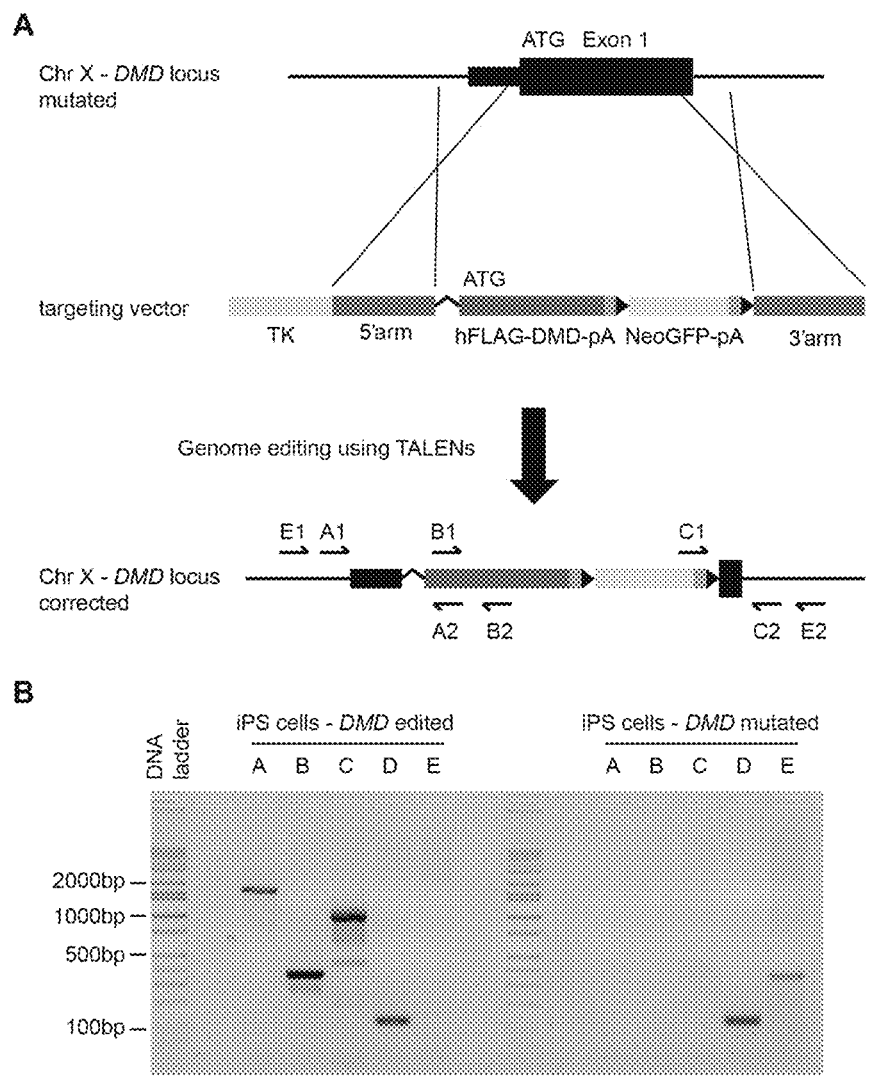
FIG. 4 provides a schematic representation of the strategy used to correct DMD iPS cells. A) DMD locus correction mediated by TALENs effectors and homologous recombination vector. Correction was made in the Exon 1 of the Dystrophin gene. B) PCRs analysis to confirm the correction in the DMD clones. 5 different couples of primers were synthetized to confirm a positive and negative selection of the clone corrected. PCRs A-B-C were used as a positive selection and are specific only for the corrected clone. PCR D was made on exon 9 of Dystrophin gene and it was used as an internal control for the quality of the genomic DNA extracted. Primers made for PCR E are used for the negative selection and the PCR's amplicon was detected only in the DMD. The 5 different PCRs confirmed the locus specific integration on DMD Exon 1 of the homologous recombination vector.

The targeting vector encoding the full length (FL) DYS-TROPHIN and validated TALENs were co-transfected into DMD iPS cells. After 10 days in selection with G418 (50 ng/ml), resistant clones were picked and were grown for 5 days with GANC (2 μM/ml). Corrected iPS clones were transduced with Pax7 to derive Pax7+ skeletal myogenic progenitors (FIG. 3A, left panel), which when switched into differentiation conditions, differentiated into MyoG+ and MHC+ myotubes (FIG. 3). Effective gene targeting at the DMD locus in corrected DMD clones was verified by PCR at various regions (FIG. 4B).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What we claim is:

1. An in vitro method to correct a dysfunctional gene, wherein the dysfunction is caused by a genetic mutation, the method comprising: introducing one or more nucleic acids encoding a TALEN and a nucleic acid donor sequence into a cell comprising said dysfunctional gene, wherein the TALEN comprises a plurality of TAL effector sequences that can bind to a target site of insertion in the dysfunctional gene, wherein said nucleic acid donor sequence comprises a stop codon and a nucleic acid encoding a wild-type, functional coding region of said dysfunctional gene flanked by sequences homologous to the target site of insertion, wherein the cell expresses said TALEN and said TALEN introduces a site-specific double stranded break at the target site of insertion in said dysfunctional gene, thereby introducing a stop codon into the dysfunctional gene in the cell and introducing a wild-type, functional coding region of said dysfunctional gene into said cell.

2. The method of claim 1, wherein the cell is a fibroblast, keratinocyte, induced pluripotent stem cell, hematopoietic stem cell, mesenchymal stem cell, embryonic stem cell, hematopoietic progeny cell, glia cell, neural cell, neuroglial progenitor cell, neuroglial stem cell, muscle cell, lung cell, pancreatic, liver cell and/or a cell of the reticular endothelial system.

3. The method of claim 2, wherein the cell is a muscle cell.

4. The method of claim 1, wherein the TALEN is encoded by a nucleic acid having the sequence of 5'-ATACACTTTTCAAAATGCTT-spacer-AGAGGACTGTTG-TAAGTAC-3' (SEQ ID NOs:5 and 6) and/or a nucleic acid sequence comprising 5'-ATATTTTACTGTGGCATAACGT-spacer-AATTAGGTAGATTGATTTTAAATTATCAC-3' (SEQ ID NOs:9 and 10).

5. The method of claim 1, wherein said one or more nucleic acids are part of a vector or plasmid.

6. The method of claim 1, wherein the dysfunctional gene is a dysfunctional form of a gene encoding DMD, CFTR, DYSF, EMD, LMNA, TTID, CAV3, DNAJB6, DES, TNPO3, CAPN3, SGCG, SGCA, ANO5, SGCB, SGCD, TCAP, TRIM32, FKRP, TTN, POMT1, FKTN, POMT2, POMGNT1, PLEC1, or HBB.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
agcaggaaaa catgtcccat                                                  20

<210> SEQ ID NO 2
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 2
tttgaaaagt gtatatcaag gc                                               22

<210> SEQ ID NO 3
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 3
agtagtttgc aaagaagcat aa                                               22

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 4
gagataaact cccatctctt                                                  20

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
atacactttt caaaatgctt                                                  20

<210> SEQ ID NO 6
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 6
agaggactgt tgtaagtac                                                   19

<210> SEQ ID NO 7
<211> LENGTH: 40
<212> TYPE: PRT
<213> ORGANISM: Artificial Sequence
<220> FEATURE:
<223> OTHER INFORMATION: A synthetic oligopeptide

<400> SEQUENCE: 7

Asn Ile Asn Gly Asn Ile His Asp Asn Ile His Asp Asn Gly Asn Gly
 1               5                  10                  15

Asn Gly Asn Gly His Asp Asn Ile Asn Ile Asn Ile Asn Ile Asn Gly
            20                  25                  30

Asn Asn His Asp Asn Gly Asn Gly
          35                  40

<210> SEQ ID NO 8
<211> LENGTH: 38
<212> TYPE: PRT
<213> ORGANISM: Artificial Sequence
<220> FEATURE:
<223> OTHER INFORMATION: A synthetic oligopeptide

<400> SEQUENCE: 8

Asn Asn Asn Gly Asn Ile His Asp Asn Gly Asn Gly Asn Ile His Asp
1               5                   10                  15

Asn Ile Asn Ile His Asp Asn Ile Asn Asn Gly His Asp His Asp
            20                  25                  30

Asn Gly His Asp Asn Gly
         35

<210> SEQ ID NO 9
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 9 atatttact gtggcataac gt                                         22

<210> SEQ ID NO 10
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 10
aattaggtag attgatttta aattatcac                                 29

<210> SEQ ID NO 11
<211> LENGTH: 44
<212> TYPE: PRT
<213> ORGANISM: Artificial Sequence
<220> FEATURE:
<223> OTHER INFORMATION: A synthetic oligopeptide

<400> SEQUENCE: 11

Asn Ile Asn Gly Asn Ile Asn Gly Asn Gly Asn Gly Asn Gly Asn Ile
1               5                   10                  15

His Asp Asn Gly Asn Asn Asn Gly Asn Asn Asn Asn His Asp Asn Ile
            20                  25                  30

Asn Gly Asn Ile Asn Ile His Asp Asn Asn Asn Gly
         35                  40

<210> SEQ ID NO 12
<211> LENGTH: 58
<212> TYPE: PRT
<213> ORGANISM: Artificial Sequence
<220> FEATURE:
<223> OTHER INFORMATION: A synthetic oligopeptide

<400> SEQUENCE: 12

Asn Asn Asn Gly Asn Asn Asn Ile Asn Gly Asn Ile Asn Ile Asn Gly
1               5                   10                  15

Asn Gly Asn Gly Asn Ile Asn Ile Asn Ile Asn Ile Asn Gly His Asp

```
                        20                  25                  30
Asn Ile Asn Ile Asn Gly His Asp Asn Gly Asn Ile His Asp His Asp
                35                  40                  45

Asn Gly Asn Ile Asn Ile Asn Gly Asn Gly
        50                  55
```

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 13
aattggcacc agagaaatgg                                           20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
tctcgacaag cccagtttct                                           20

<210> SEQ ID NO 15
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 15
tcttttaatg atctagaacc gg                                        22

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
aatcctacag ggcatgtccc                                           20

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 17
ttctaagttt gggaagcagc a                                         21

<210> SEQ ID NO 18
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 18
ggtctggcct atgactatgg a                                         21

-continued

<210> SEQ ID NO 19
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 19
gcagtggcga agcacttt                                                  18

<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20
acaatagagt tggttggggg                                                20

<210> SEQ ID NO 21
<211> LENGTH: 9068
<212> TYPE: DNA
<213> ORGANISM: Artificial Sequence
<220> FEATURE:
<223> OTHER INFORMATION: A synthetic oligonucleotide

<400> SEQUENCE: 21
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
ggccatcgcc ctgatagacg ttttttcgcc ctttgacgtt ggagtccacg ttctttaata     300
gtggactctt gttccaaact ggaacaacac tcaaccctat ctcggtctat tcttttgatt     360
tataagggat tttgccgatt tcggcctatt ggttaaaaaa tgagctgatt taacaaaaat     420
ttaacgcgaa ttttaacaaa atattaacgc ttacaatttg ccattcgcca ttcaggctgc     480
gcaactgttg ggaagggcga tcggtgcggg cctcttcgct attacgccag ctggcgaaag     540
ggggatgtgc tgcaaggcga ttaagttggg taacgccagg gttttcccag tcacgacgtt     600
gtaaaacgac ggccagtgaa ttgtaatacg actcactata gggcgaccca gctttctag      660
agtcgagcag tgtggttttc aagaggaagc aaaaagcctc tccacccagg cctggaatgt     720
ttccacccaa tgtcgagcag tgtggttttg caagaggaag caaaaagcct ctccacccag     780
gcctggaatg tttccaccca atgtcgagca accccgccc agcgtcttgt cattggcgaa      840
ttcgaacacg cagatgcagt cggggcggcg cggtcccagg tccacttcgc atattaaggt     900
gacgcgtgtg gcctcgaaca ccgagcgacc ctgcagcgac ccgcttaaca gcgtcaacag     960
cgtgccgcag atcttggtgg cgtgaaactc ccgcacctct tcggccagcg ccttgtagaa    1020
gcgcgtatgg cttcgtaccc cggccatcag cacgcgtctg cgttcgacca ggctgcgcgt    1080
tctcgcggcc atagcaaccg acgtacgcg ttgcgccctc gccggcagca agaagccacg    1140
gaagtccgcc cggagcagaa aatgcccacg ctactgcggg tttatataga cggtccccac    1200
gggatgggga aaaccaccac cacgcaactg ctggtggccc tgggttcgcg cgacgatatc    1260
gtctacgtac ccgagccgat gacttactgg cgggtgctgg ggcttccga dacaatcgcg    1320

```
aacatctaca ccacacaaca ccgccttgac cagggtgaga tatcggccgg ggacgcggcg   1380
gtggtaatga caagcgccca gataacaatg ggcatgcctt atgccgtgac cgacgccgtt   1440
ctggctcctc atatcggggg ggaggctggg agctcacatg ccccgccccc ggccctcacc   1500
ctcatcttcg accgccatcc catcgccgcc ctcctgtgct acccgccgc gcgatacctt    1560 atgggcagca tgaccccca ggccgtgctg gcgttcgtgg ccctcatccc gccgaccttg    1620
cccggcacaa acatcgtgtt gggggcccctt ccggaggaca gacacatcga ccgcctggcc   1680
aaacgccagc gccccggcga gcggcttgac ctggctatgc tggccgcgat tcgccgcgtt   1740
tacgggctgc ttgccaatac ggtgcggtat ctgcagggcg gcgggtcgtg gcgggaggat   1800
tggggacagc tttcggggac ggccgtgccg ccccagggtg ccgagcccca gagcaacgcg   1860
ggcccacgac cccatatcgg ggacacgtta tttaccctgt ttcgggcccc cgagttgctg   1920
gcccccaacg gcgacctgta caacgtgttt gcctgggcct tggacgtctt ggccaaacgc   1980
ctccgtccca tgcacgtctt tatcctggat tacgaccaat cgcccgccgg ctgccgggac   2040
gccctgctgc aacttacctc cgggatgatc cagacccacg tcaccacccc aggctccata   2100
ccgacgatct gcgacctggc gcgcacgttt gcccgggaga tggggaggc taactgaaac    2160 acggaaggag acaataccgg aaggaacccg cgctatgacg gcaataaaaa gacagaacag   2220
catgataaga tacattgatg agtttggaca aaccacaact agaatgcagt gaaaaaaatg   2280
ctttatttgt gaaatttgtg atgctattgc tttatttgtg aaatttgtga tgctattgct   2340
ttatttgtaa ccattataag ctgcaataaa caagttaaca acaacaattg cattcatttt   2400
atgtttcagg ttcaggggga ggtgtgggag gttttttaaa gcaagtaaaa cctctacaaa   2460
tgtggtagat ccatttaaat gttaattaaa gcaggaaaac atgtcccatg agacctatac   2520
acacacacat tctgccttca gaattcagct gctgcattct gctgctgctt ctcttattca   2580
gactgttggc atcatcaata cataactttt gattgaatcc caaggggaaa aaataacttt   2640
ggtagacagt ggatacataa caaatgcatg gattattctg ggcattcctt tttatttggt   2700
agagtgaaat ttttggtgtt gttgagagga taaaaaaggc atttaaaagt caattttgaa   2760
tccggatttt ctgctctgtt aataaattca catgaaagtt acagaaagta ttgttatgct   2820
tttgtactga atagtttttg tgtttagaag gctttaaaag caagtactat gtccactgtg   2880
ctattctggt ttggatatta atcagaacac agttgagcat tgtttgaatt cacagagctt   2940
gccatgctgg aagcacaacc ttatatgtag tgaccatgga cagtcctatt atgggaaacc   3000
aacttgagag agaaggcggg tcacttgctt gtgcgcaggt cctggaattt gaaatatccg   3060
ggggcctcta cagaatcctg gcatcagtta ctgtgttgac tcactcagtg ttgggatcac   3120
tcactttccc cctacaggac tcagatctgg gaggcaatta ccttcggaga aaacgaata    3180 ggaaaaactg aagtgttact ttttttaaag ctgctgaagt ttgttggttt ctcattgttt   3240
ttaagcctac tggagcaata aagtttgaag aacttttacc aggttttttt tatcgctgcc   3300
ttgatataca cttttcaaag taagtatcaa ggttacaaga caggtttaag gagaccaata   3360
gaaactgggc ttgtcgagac agagaagact cttgcgtttc tgataggcac ctattggtct   3420
tactgacatc cactttgcct ttctctccac agctcgagtc tagcggccgc cagcatgata   3480
agatacattg atgagtttgg acaaaccaca actagaatgc agtgaaaaaa atgctttatt   3540
tgtgaaattt gtgatgctat tgctttattt gtgaaatttg tgatgctatt gctttatttg   3600
taaccattat aagctgcaat aaacaagtta acaacaacaa ttgcattcat tttatgtttc   3660
aggttcaggg ggaggtgtgg gaggtttttt aaagcaagta aaacctctac aaatgtggta   3720
```

```
gatccattta aatgttaatt aaataacttc gtatagcata cattatacga agttatggat    3780
ctgcgatcgc tccggtgccc gtcagtgggc agagcgcaca tcgcccacag tccccgagaa    3840
gttgggggga ggggtcggca attgaaccgg tgcctagaga aggtggcgcg gggtaaactg    3900
ggaaagtgat gtcgtgtact ggctccgcct ttttcccgag ggtgggggag aaccgtatat    3960
aagtgcagta gtcgccgtga acgttctttt tcgcaacggg tttgccgcca gaacacagct    4020
ggtgggtagg gatgagggag ggaggggcat tgtgatgtac agggctgctc tgtgagatca    4080
agggtctctt aagggtggga gctggggcag ggactacgag agcagccaga tgggctgaaa    4140
gtggaactca aggggtttct ggcacctacc tacctgcttc ccgctggggg gtggggagtt    4200
ggcccagagt cttaagattg gggcagggtg gagaggtggg ctcttcctgc ttcccactca    4260
tcttatagct ttctttcccc agatccgaat tcgagatcca aaccaaggag gaaaggatat    4320
cacagaggag accatggtga gcaagggcga ggagctgttc accggggtgg tgcccatcct    4380
ggtcgagctg gacggcgacg taaacggcca caagttcagc gtgtctggcg agggcgaggg    4440
cgatgccacc tacggcaagc tgaccctgaa gttcatctgc accaccggca agctgcccgt    4500
gccctggccc accctcgtga ccaccctgac ctacggcgtg cagtgcttca gccgctaccc    4560
cgaccacatg aagcagcacg acttcttcaa gtccgccatg cccgaaggct acgtccagga    4620
gcgcaccatc ttcttcaagg acgacggcaa ctacaagacc cgcgccgagg tgaagttcga    4680
gggcgacacc ctggtgaacc gcatcgagct gaagggcatc gacttcaagg aggacggcaa    4740
catcctgggg cacaagctgg agtacaacta caacagccac aacgtctata tcatggccga    4800
caagcagaag aacggcatca aggcgaactt caagatccgc cacaacatcg aggacggcag    4860
cgtgcagctc gccgaccact accagcagaa caccccatc ggcgacggcc ccgtgctgct    4920
gcccgacaac cactacctga gcacccagtc cgccctgagc aaagacccca acgagaagcg    4980
cgatcacatg gtcctgctgg agttcgtgac cgccgccggg atcactctcg gcatggacga    5040
gctgtacaag ggaagagccg agggcagggg aagtcttcta acatgcgggg acgtggagga    5100
aaatcccggg cccggaatcg aacaagacgg cctccatgct ggcagtcccg cagcttgggt    5160
cgaacgcttg ttcgggtacg actgggccca gcagaccatc ggatgtagcg atgcggccgt    5220
gttccgtcta agcgctcaag gccggcccgt gctgttcgtg aagaccgacc tgagcggcgc    5280
cctgaacgag cttcaagacg aggctgcccg cctgagctgg ctggccacca ccggcgtacc    5340
ctgcgccgct gtgttggatg ttgtgaccga agccggccgg gactggctgc tgctgggcga    5400
ggtccctggc caggatctgc tgagcagcca ccttgccccc gctgagaagg tttctatcat    5460
ggccgatgca atgcggcgcc tgcacaccct ggaccccgct acctgcccct tcgaccacca    5520
ggctaagcat cggatcgagc gtgctcggac ccgcatggag gccggcctgg tggaccagga    5580
cgacctggac gaggagcatc agggcctggc cccgctgaa ctgttcgccc gactgaaagc    5640
ccgcatgccg gacggtgagg acctggttgt cacacacgga gatgcctgcc tccctaacat    5700
catggtcgag aatggccgct tctccggctt catcgactgc ggtcgcctag agttgccga    5760
ccgctaccag gacatcgccc tggccacccg cgacatcgct gaggagcttg gcggcgagtg    5820
ggccgaccgc ttcttagtct tgtacggcat cgcagctccc gacagccagc gcatcgcctt    5880
ctaccgcttg ctcgacgagt tcttttaatg atctagaacc ggtcatggcc gcaataaaat    5940
atctttattt tcattacatc tgtgtgttgg ttttttgtgt gcaataaaat aacttcgtat    6000
agcatacatt atacgaagtt atagtagttt gcaaagaagc ataaatgtta tatatactgc    6060
```

```
atatatatat gtatttattc aggaatatat attttttcatt gggaaaactt ttcaacagaa    6120
atggagtgta aaagtttttc tttgcgatag aactaaacac atgatttctt gattaacaaa    6180
ccactgcagt aatagaatat gcagaatgtc atttgactat aacagattta ttttgattgc    6240
tgtgagatag tttgtatatc tgagttatta ttttgattag ttgatacttc cgtatttagt    6300
aacagttaca taaaggttac tgacctgaca tatattctca attgaactaa ctactgtata    6360
ggaactacat ggaggcctaa aagttagaaa aagtttctct gacacatcat ggataaaata    6420
aagaataaaa tgagttggga cggataattg aaggatgtga aaagtattga taaagattta    6480
attttaatgt ttcttactca catttactat ttcaaatgct cttttctgta gcatatcatg    6540
ataattattt caaataatga tgtgatctat gctatcaaat gatcagatga tttcttgggt    6600
aaacgacata caaacttgag gaactcctaa ttatatttag tagtaaagtc accttgttgt    6660
ttcatgtcta ttatgagcca gcttttcagt tcaattttt  agtttgtctt tcatatagaa    6720
atacaactat ttcgtttatt tttaagaaag tcatgatgac taatgaagga tttaaaaatg    6780
gactgtggca caacagtaaa aataatatat gataaggact gtgtgtcccg aagagatggg    6840
agtttatctc tagaggatcc ggggatatcc tcgaggttcc ctttagtgag ggttaattgc    6900
gagcttggcg taatcatggt catagctgtt tcctgtgtga aattgttatc cgctcacaat    6960
tccacacaac atacgagccg gaagcataaa gtgtaaagcc tggggtgcct aatgagtgag    7020
ctaactcaca ttaattgcgt tgcgctcact gcccgctttc cagtcgggaa acctgtcgtg    7080
ccagctgcat taatgaatcg gccaacgcgc ggggagaggc ggtttgcgta ttgggcgctc    7140
ttccgcttcc tcgctcactg actcgctgcg ctcggtcgtt cggctgcggc gagcggtatc    7200
agctcactca aaggcggtaa tacggttatc cacagaatca ggggataacg caggaaagaa    7260
catgtgagca aaaggccagc aaaaggccag gaaccgtaaa aaggccgcgt tgctggcgtt    7320
tttccatagg ctccgccccc ctgacgagca tcacaaaaat cgacgctcaa gtcagaggtg    7380
gcgaaacccg acaggactat aaagatacca ggcgtttccc cctggaagct ccctcgtgcg    7440
ctctcctgtt ccgaccctgc cgcttaccgg atacctgtcc gcctttctcc cttcgggaag    7500
cgtggcgctt tctcatagct cacgctgtag gtatctcagt tcggtgtagg tcgttcgctc    7560
caagctgggc tgtgtgcacg aaccccccgt tcagcccgac cgctgcgcct tatccggtaa    7620
ctatcgtctt gagtccaacc cggtaagaca cgacttatcg ccactggcag cagccactgg    7680
taacaggatt agcagagcga ggtatgtagg cggtgctaca gagttcttga agtggtggcc    7740
taactacggc tacactagaa gaacagtatt tggtatctgc gctctgctga agccagttac    7800
cttcggaaaa agagttggta gctcttgatc cggcaaacaa accaccgctg gtagcggtgg    7860
tttttttgtt tgcaagcagc agattacgcg cagaaaaaaa ggatctcaag aagatccttt    7920
gatcttttct acggggtctg acgctcagtg gaacgaaaac tcacgttaag ggattttggt    7980
catgagatta tcaaaaagga tcttcaccta gatcctttta aattaaaaat gaagttttaa    8040
atcaatctaa agtatatatg agtaaacttg gtctgacagt taccaatgct taatcagtga    8100
ggcacctatc tcagcgatct gtctatttcg ttcatccata gttgcctgac tccccgtcgt    8160
gtagataact acgatacggg agggcttacc atctggcccc agtgctgcaa tgataccgcg    8220
agacccacgc tcaccggctc cagatttatc agcaataaac cagccagccg aagggccga    8280 gcgcagaagt ggtcctgcaa ctttatccgc ctccatccag tctattaatt gttgccggga    8340
agctagagta agtagttcgc cagttaatag tttgcgcaac gttgttgcca ttgctacagg    8400
catcgtggtg tcacgctcgt cgtttggtat ggcttcattc agctccggtt cccaacgatc    8460
```

-continued

```
aaggcgagtt acatgatccc ccatgttgtg caaaaaagcg gttagctcct tcggtcctcc   8520
gatcgttgtc agaagtaagt tggccgcagt gttatcactc atggttatgg cagcactgca   8580
taattctctt actgtcatgc catccgtaag atgctttttct gtgactggtg agtactcaac   8640
caagtcattc tgagaatagt gtatgcggcg accgagttgc tcttgcccgg cgtcaatacg   8700
ggataatacc gcgccacata gcagaacttt aaaagtgctc atcattggaa aacgttcttc   8760
ggggcgaaaa ctctcaagga tcttaccgct gttgagatcc agttcgatgt aacccactcg   8820
tgcacccaac tgatcttcag catcttttac tttcaccagc gtttctgggt gagcaaaaac   8880
aggaaggcaa aatgccgcaa aaagggaat aagggcgaca cggaaatgtt gaatactcat   8940
actcttcctt tttcaatatt attgaagcat ttatcagggt tattgtctca tgagcggata   9000
catatttgaa tgtatttaga aaataaaca aataggggtt ccgcgcacat ttccccgaaa   9060
agtgccac                                                            9068
```

<210> SEQ ID NO 22
<211> LENGTH: 6436
<212> TYPE: DNA
<213> ORGANISM: Homo sapiens

<400> SEQUENCE: 22

```
tttcctgcgt tatccctga ttctgtggat aaccgtatta ccgcctttga gtgagctgat     60
accgctcgcc gcagccgaac gaccgagcgc agcgagtcag tgagcgagga agcggaagag    120
cgcccaatac gcaaaccgcc tctccccgcg cgttggccga ttcattaatg cagctggcac    180
gacaggtttc ccgactggaa agcgggcagt gagcgcaacg caattaatac gcgtaccgct    240
agccaggaag agtttgtaga aacgcaaaaa ggccatccgt caggatggcc ttctgcttag    300
tttgatgcct ggcagtttat ggcgggcgtc ctgcccgcca ccctccgggc cgttgcttca    360
caacgttcaa atccgctccc ggcggatttg tcctactcag gagagcgttc accgacaaac    420
aacagataaa acgaaaggcc cagtcttccg actgagcctt tcgttttatt tgatgcctgg    480
cagttcccta ctctcgcgtt aacgctagca tggatgtttt cccagtcacg acgttgtaaa    540
acgacggcca gtcttaagct cgggcccaa ataatgattt tattttgact gatagtgacc    600
tgttcgttgc aacaaattga tgagcaatgc ttttttataa tgccaacttt gtacaaaaaa    660
gcaggctcaa gggccgtcaa ggccaccat ggactacaag gacgacgatg acaagctttg    720
gtgggaagaa gtagaggact gttatgaaag agaagatgtt caaaagaaaa cattcacaaa    780
atgggtaaat gcacaatttt ctaagtttgg gaagcagcat attgagaacc tcttcagtga    840
cctacaggat gggaggcgcc tcctagacct cctcgaaggc ctgacagggc aaaaactgcc    900
aaaagaaaaa ggatccacaa gagttcatgc cctgaacaat gtcaacaagg cactgcgggt    960
tttgcagaac aataatgttg atttagtgaa tattggaagt actgacatcg tagatggaaa   1020
tcataaactg actcttggtt tgatttggaa tataatcctc cactggcagg tcaaaaatgt   1080
aatgaaaaat atcatggctg gattgcaaca aaccaacagt gaaaagattc tcctgagctg   1140
ggtccgacaa tcaactcgta attatccaca ggttaatgta atcaacttca ccaccagctg   1200
gtctgatggc ctggctttga atgctctcat ccatagtcat aggccagacc tatttgactg   1260
gaatagtgtg gtttgccagc agtcagccac acaacgactg gaacatgcat tcaacatcgc   1320
cagatatcaa ttaggcatag agaaactact cgatcctgaa gatgttgata ccacctatcc   1380
agataagaag tccatcttaa tgtacatcac atcactcttc caagtttttgc ctcaacaagt   1440
```

```
gagcattgaa gccatccagg aagtggaaat gttgccaagg ccacctaaag tgactaaaga    1500
agaacatttt cagttacatc atcaaatgca ctattctcaa cagatcacgg tcagtctagc    1560
acagggatat gagagaactt cttcccctaa gcctcgattc aagagctatg cctacacaca    1620
ggctgcttat gtcaccacct ctgacccfac acggagccca tttccttcac agcatttgga    1680
agctcctgaa gacaagtcat ttggcagttc attgatggag agtgaagtaa acctggaccg    1740
ttatcaaaca gctttagaag aagtattatc gtggcttctt tctgctgagg acacattgca    1800
agcacaagga gagatttcta atgatgtgga agtggtgaaa gaccagtttc atactcatga    1860
ggggtacatg atggatttga cagcccatca gggccgggtt ggtaatattc tacaattggg    1920
aagtaagctg attggaacag gaaaattatc agaagatgaa gaaactgaag tacaagagca    1980
gatgaatctc ctaaattcaa gatgggaatg cctcagggta gctagcatgg aaaaacaaag    2040
caatttacat agagttttaa tggatctcca gaatcagaaa ctgaaagagt tgaatgactg    2100
gctaacaaaa acagaagaaa gaacaaggaa aatggaggaa gagcctcttg gacctgatct    2160
tgaagaccta aaacgccaag tacaacaaca taaggtgctt caagaagatc tagaacaaga    2220
acaagtcagg gtcaattctc tcactcacat ggtggtggta gttgatgaat ctagtggaga    2280
tcacgcaact gctgctttgg aagaacaact taaggtattg ggagatcgat gggcaaacat    2340
ctgtagatgg acagaagacc gctgggttct tttacaagac atccttctca aatggcaacg    2400
tcttactgaa gaacagtgcc tttttagtgc atggcttttca gaaaagaag atgcagtgaa    2460 caagattcac acaactggct ttaaagatca aaatgaaatg ttatcaagtc ttcaaaaact    2520
ggccgtttta aaagcggatc tagaaaagaa aaagcaatcc atgggcaaac tgtattcact    2580
caaacaagat cttcttcaa cactgaagaa taagtcagtg acccagaaga cggaagcatg    2640
gctggataac tttgcccggt gttgggataa tttagtccaa aaacttgaaa agagtacagc    2700
acagatttca caggctgtca ccaccactca gccatcacta acacagacaa ctgtaatgga    2760
aacagtaact acggtgacca caagggaaca gatcctggta aagcatgctc aagaggaact    2820
tccaccacca cctccccaaa agaagaggca gattactgtg gatcttgaaa gactccagga    2880
acttcaagag gccacggatg agctggacct caagctgcgc caagctgagg tgatcaaggg    2940
atcctggcag cccgtgggcg atctcctcat tgactctctc caagatcacc tcgagaaagt    3000
caaggcactt cgaggagaaa ttgcgcctct gaaagagaac gtgagccacg tcaatgacct    3060
tgctcgccag cttaccactt tgggcattca gctctcaccg tataacctca gcactctgga    3120
agacctgaac accagatgga gcttctgca ggtggccgtc gaggaccgag tcaggcagct    3180
gcatgaagcc cacagggact ttggtccagc atctcagcac tttctttcca cgtctgtcca    3240
gggtccctgg gagagagcca tctcgccaaa caaagtgccc tactatatca accacgagac    3300
tcaaacaact tgctgggacc atcccaaaat gacagagctc taccagtctt tagctgacct    3360
gaataatgtc agattctcag cttataggac tgccatgaaa ctccgaagac tgcagaaggc    3420
cctttgcttg gatctcttga gcctgtcagc tgcatgtgat gccttggacc agcacaacct    3480
caagcaaaat gaccagccca tggatatcct gcagattatt aattgtttga ccactattta    3540
tgaccgcctg gagcaagagc acaacaattt ggtcaacgtc cctctctgcg tggatatgtg    3600
tctgaactgg ctgctgaatg tttatgatac gggacgaaca gggaggatcc gtgtcctgtc    3660
ttttaaaact ggcatcattt ccctgtgtaa agcacatttg gaagacaagt acagatacct    3720
tttcaagcaa gtggcaagtt caacaggatt ttgtgaccag cgcaggctgg gcctccttct    3780
gcatgattct atccaaattc aagacagtt gggtgaagtt gcatcctttg ggggcagtaa    3840
```

```
cattgagcca agtgtccgga gctgcttcca atttgctaat aataagccag agatcgaagc    3900
ggccctcttc ctagactgga tgagactgga accccagtcc atggtgtggc tgcccgtcct    3960
gcacagagtg gctgctgcag aaactgccaa gcatcaggcc aaatgtaaca tctgcaaaga    4020
gtgtccaatc attggattca ggtacaggag tctaaagcac tttaattatg acatctgcca    4080
aagctgcttt ttttctggtc gagttgcaaa aggccataaa atgcactatc ccatggtgga    4140
atattgcact ccgactacat caggagaaga tgttcgagac tttgccaagg tactaaaaaa    4200
caaatttcga accaaaaggt attttgcgaa gcatcccgga atgggctacc tgccagtgca    4260
gactgtctta gagggggaca acatggaaac tgacacaatg tgactcatgg gccgacccag    4320
cttcttgta caaagttggc attataagaa agcattgctt atcaatttgt tgcaacgaac     4380
aggtcactat cagtcaaaat aaaatcatta tttgccatcc agctgatatc ccctatagtg    4440
agtcgtatta catggtcata gctgtttcct ggcagctctg gcccgtgtct caaaatctct    4500
gatgttacat tgcacaagat aaaaatatat catcatgcct cctctagacc agccaggaca    4560
gaaatgcctc gacttcgctg ctacccaagg ttgccgggtg acgcacaccg tggaaacgga    4620
tgaaggcacg aacccagtgg acataagcct gttcggttcg taagctgtaa tgcaagtagc    4680
gtatgcgctc acgcaactgg tccagaacct tgaccgaacg cagcggtggt aacggcgcag    4740
tggcggtttt catggcttgt tatgactgtt tttttgggt acagtctatg cctcgggcat     4800
ccaagcagca agcgcgttac gccgtgggtc gatgtttgat gttatggagc agcaacgatg    4860
ttacgcagca gggcagtcgc cctaaaacaa agttaaacat catgagggaa gcggtgatcg    4920
ccgaagtatc gactcaacta tcagaggtag ttggcgtcat cgagcgccat ctcgaaccga    4980
cgttgctggc cgtacatttg tacggctccg cagtggatgg cggcctgaag ccacacagtg    5040
atattgattt gctggttacg gtgaccgtaa ggcttgatga acaacgcgg cgagctttga     5100
tcaacgacct tttggaaact tcggcttccc ctggagagag cgagattctc cgcgctgtag    5160
aagtcaccat tgttgtgcac gacgacatca ttccgtggcg ttatccagct aagcgcgaac    5220
tgcaatttgg agaatggcag cgcaatgaca ttcttgcagg tatcttcgag ccagccacga    5280
tcgacattga tctggctatc ttgctgacaa aagcaagaga acatagcgtt gccttggtag    5340
gtccagcggc ggaggaactc tttgatccgg ttcctgaaca ggatctattt gaggcgctaa    5400
atgaaaccct aacgctatgg aactcgccgc ccgactgggc tggcgatgag cgaaatgtag    5460
tgcttacgtt gtcccgcatt tggtacagcg cagtaaccgg caaaatcgcg ccgaaggatg    5520
tcgctgccga ctgggcaatg gagcgcctgc cggcccagta tcagcccgtc atacttgaag    5580
ctagacaggc ttatcttgga caagaagaag atcgcttggc ctcgcgcgca gatcagttgg    5640
aagaatttgt ccactacgtg aaaggcgaga tcaccaaggt agtcggcaaa taaccctcga    5700
gccacccatg accaaaatcc cttaacgtga gttacgcgtc gttccactga gcgtcagacc    5760
ccgtagaaaa gatcaaagga tcttcttgag atccttttt tctgcgcgta atctgctgct     5820
tgcaaacaaa aaaaccaccg ctaccagcgg tggtttgttt gccggatcaa gagctaccaa    5880
ctcttttcc gaaggtaact ggcttcagca gagcgcagat accaaatact gtccttctag     5940
tgtagccgta gttaggccac cacttcaaga actctgtagc accgcctaca tacctcgctc    6000
tgctaatcct gttaccagtg gctgctgcca gtggcgataa gtcgtgtctt accgggttgg    6060
actcaagacg atagttaccg gataaggcgc agcggtcggg ctgaacgggg ggttcgtgca    6120
cacagcccag cttggagcga acgacctaca ccgaactgag atacctacag cgtgagcatt    6180
```

| | |
|---|---|
| gagaaagcgc cacgcttccc gaagggagaa aggcggacag gtatccggta agcggcaggg | 6240 |
| tcggaacagg agagcgcacg agggagcttc caggggaaaa cgcctggtat ctttatagtc | 6300 |
| ctgtcgggtt tcgccacctc tgacttgagc gtcgattttt gtgatgctcg tcaggggggc | 6360 |
| ggagcctatg gaaaaacgcc agcaacgcgg ccttttttacg gttcctggcc ttttgctggc | 6420 |
| cttttgctca catgtt | 6436 |

<210> SEQ ID NO 23
<211> LENGTH: 830
<212> TYPE: DNA
<213> ORGANISM: Artificial Sequence
<220> FEATURE:
<223> OTHER INFORMATION: A synthetic oligonucleotide

<400> SEQUENCE: 23

| | |
|---|---|
| agcaggaaaa catgtcccat gagacctata cacacacaca ttctgccttc agaattcagc | 60 |
| tgctgcattc tgctgctgct tctcttattc agactgttgg catcatcaat acataacttt | 120 |
| tgattgaatc ccaaggggaa aaataacttt tggtagacag tggatacata acaaatgcat | 180 |
| ggattattct gggcattcct ttttatttgg tagagtgaaa tttttggtgt tgttgagagg | 240 |
| ataaaaaagg catttaaaag tcaattttga atccggattt tctgctctgt taataaattc | 300 |
| acatgaaagt tacagaaagt attgttatgc ttttgtactg aatagttttt gtgtttagaa | 360 |
| ggctttaaaa gcaagtacta tgtccactgt gctattctgg tttggatatt aatcagaaca | 420 |
| cagttgagca ttgtttgaat tcacagagct tgccatgctg gaagcacaac cttatatgta | 480 |
| gtgaccatgg acagtcctat tatgggaaac caacttgaga gagaaggcgg gtcacttgct | 540 |
| tgtgcgcagg tcctggaatt tgaaatatcc gggggcctct acagaatcct ggcatcagtt | 600 |
| actgtgttga ctcactcagt gttgggatca ctcactttcc ccctacagga ctcagatctg | 660 |
| ggaggcaatt accttcggag aaaaacgaat aggaaaaact gaagtgttac ttttttttaaa | 720 |
| gctgctgaag tttgttggtt tctcattgtt tttaagccta ctggagcaat aaagtttgaa | 780 |
| gaacttttac caggtttttt ttatcgctgc cttgatatac acttttcaaa | 830 |

<210> SEQ ID NO 24
<211> LENGTH: 828
<212> TYPE: DNA
<213> ORGANISM: Artificial Sequence
<220> FEATURE:
<223> OTHER INFORMATION: A synthetic oligonucleotide

<400> SEQUENCE: 24

| | |
|---|---|
| agtagtttgc aaagaagcat aaatgttata tatactgcat atatatatgt atttattcag | 60 |
| gaatatatat ttttcattgg gaaaacttttt caacagaaat ggagtgtaaa agttttttctt | 120 |
| tgcgatagaa ctaaacacat gatttcttga ttaacaaacc actgcagtaa tagaaatatgc | 180 |
| agaatgtcat ttgactataa cagatttatt ttgattgctg tgagatagtt tgtatatctg | 240 |
| agttattatt ttgattagtt gatacttccg tatttagtaa cagttacata aaggttactg | 300 |
| acctgacata tattctcaat tgaactaact actgtatagg aactacatgg aggcctaaaa | 360 |
| gttagaaaaa gttctctga cacatcatgg ataaaataaa gaataaaatg agttgggacg | 420 |
| gataattgaa ggatgtgaaa agtattgata aagatttaat tttaatgttt cttactcaca | 480 |
| tttactattt caaatgctct tttctgtagc atatcatgat aattatttca ataatgatg | 540 |
| tgatctatgc tatcaaatga tcagatgatt tcttgggtaa acgacataca aacttgagga | 600 |
| actcctaatt atatttagta gtaaagtcac cttgttgttt catgtctatt atgagccagc | 660 |

```
ttttcagttc aatttttttag tttgtctttc atatagaaat acaactattt cgtttatttt    720
taagaaagtc atgatgacta atgaaggatt taaaaatgga ctgtggcaca acagtaaaaa    780
taatatatga taaggactgt gtgtcccgaa gagatgggag tttatctc                 828
```

<210> SEQ ID NO 25
<211> LENGTH: 4025
<212> TYPE: DNA
<213> ORGANISM: Homo sapiens

<400> SEQUENCE: 25

```
gccccaaaac aatttttttca ttttttctat gttgttttat gaaaattttg cttatatgca     60
tatttagaca accacactga gaggaaagga ggtgacctag ggaaaagaat gttttaaatt    120
aaaattaggc cttatgtttt atctcataca ccttttgctg gggaaaatag caatgttatg    180
acaataatat tctaaaacac aaaatgtaca attaactatt aaggtaaaca tcacagtctg    240
actcaatatt ttttttaattt ttatctatta ctcattgcag tcgcaagcag ttgaatgttt    300
gacatagaaa aatgagtctg tcactttaac aaatggtaca ataaaaacac tcaaacaaaa    360
attttagtag ggattattat aactataaaa agaatatctt tctttaaaaa atgttttccaa    420 tgttttctat caattttggg ctcgcctgtt gcataaaagt aataaggaac aagatgaaga    480
agctttctat tggcaaagaa tgatttacat gctgaatgac ataatacaac tgtattcact    540
taatacagaa acaagcctc  tattcagaac cattaaatga tcattaactc aatgtctaaa    600
aaaatggtgt tttaagaatt ggcaccagag aaatggaaga agaataatt tgttagtaaa    660 gaagttttag cataattcac aactgaaatt taggatttga gaaaaatttc tttcctgcat    720
tataagagta ttcttatttt tagcaggaaa acatgtccca tgagacctat acacacacac    780
attctgcctt cagaattcag ctgctgcatt ctgctgctgc ttctcttatt cagactgttg    840
gcatcatcaa tacataactt ttgattgaat cccaagggga aaaaataact ttggtagaca    900
gtggatacat aacaaatgca tggattattc tgggcattcc tttttatttg gtagagtgaa    960
atttttggtg ttgttgagag gataaaaaag gcatttaaaa gtcaattttg aatccggatt   1020
ttctgctctg ttaataaatt cacatgaaag ttacagaaag tattgttatg cttttgtact   1080
gaatagtttt tgtgtttaga aggctttaaa agcaagtact atgtccactg tgctattctg   1140
gtttggatat taatcagaac acagttgagc attgttgaa  ttcacagagc ttgccatgct   1200
ggaagcacaa ccttatatgt agtgaccatg acagtccta  ttatgggaaa ccaacttgag   1260
agagaaggcg ggtcacttgc ttgtgcgcag gtcctgaat  ttgaaatatc cgggggcctc   1320
tacagaatcc tggcatcagt tactgtgttg actcactcag tgttgggatc actcactttc   1380
cccctacagg actcagatct gggaggcaat taccttcgga gaaaaacgaa taggaaaaac   1440
tgaagtgtta ctttttttaa agctgctgaa gtttgttggt ttctcattgt ttttaagcct   1500
actggagcaa taaagtttga agaactttta ccaggttttt tttatcgctg ccttgatata   1560
cacttttcaa aatgctttgg tgggaagaag tagaggactg ttgtaagtac aaagtaacta   1620
aaaatatatt ttactgtggc ataacgttta gtttgtgaca agctcactaa ttaggtagat   1680
tgattttaaa ttatcacagt agtttgcaaa gaagcataaa tgttatatat actgcatata   1740
tatatgtatt tattcaggaa tatatatttt tcattgggaa aacttttcaa cagaaatgga   1800
gtgtaaaagt ttttctttgc gatagaacta aacacatgat ttcttgatta acaaaccact   1860
gcagtaatag aatatgcaga atgtcatttg actataacag atttatttg  attgctgtga   1920
```

-continued

```
gatagtttgt atatctgagt tattattttg attagttgat acttccgtat ttagtaacag    1980
ttacataaag gttactgacc tgacatatat tctcaattga actaactact gtataggaac    2040
tacatggagg cctaaaagtt agaaaagtt tctctgacac atcatggata aaataaagaa     2100
taaaatgagt tgggacggat aattgaagga tgtgaaaagt attgataaag atttaatttt    2160
aatgtttctt actcacattt actatttcaa atgctctttt ctgtagcata tcatgataat    2220
tatttcaaat aatgatgtga tctatgctat caaatgatca gatgatttct tgggtaaacg    2280
acatacaaac ttgaggaact cctaattata tttagtagta aagtcacctt gttgtttcat    2340
gtctattatg agccagcttt tcagttcaat tttttagttt gtctttcata tagaaataca    2400
actatttcgt ttattttaa gaaagtcatg atgactaatg aaggatttaa aaatggactg     2460
tggcacaaca gtaaaaataa tatatgataa ggactgtgtg tcccgaagag atgggagttt    2520
atctcttccc cacccatctt tgacttgtgg agtgtagtta ttctaaaata gatatgaggg    2580
caatgcctat aattaagaat gaaaaaataa atctctccaa ataagtaatg ctccacaact    2640
actaaaaaaa aaggcagaag ttttgccact gggaaaactt tgtggaaata agttaacatt    2700
gtccatgtat tgagtcacat taaaagctac cagactttat aatacaatat ttacttacat    2760
tgttggcttg cttcataaat ttcttttggt ggacatcatt attactttta gattgaaaaa    2820
ctattatatt tactatcatt acaaatatat gcatggcata tatctgttgt ttgcaatata    2880
cacacacatt tttatttttt gttttatttt ctttgatata tgtaacataa ataccatcaa    2940
aatcactagt gattttatat atatatatat tctacataat taacatcata tacaagtata    3000
tagagcaatt ttgaaagaat atatgcaatt ctgctgaaat taagcaaggt aaatctacac    3060
tctgctttgt catagatatt caaataactt tcaattctta gaatgcgaag aaaggtaatc    3120
tttttgggac atgccctgta ggatttttc acgctgcatt taaaaaatca tcaagtaatg    3180
cctatgcaac atgacaatga gtttggtaag aaaaaacgga gatatactca gggctatatt    3240
atacattaaa ttttgctgtt tgacaacata ctgctacttg gatgtttgac atttgaatcc    3300
agtttgtaaa tttgccgtag tttgataaac ttacaaaagt acgttttgtt gttttttaac    3360
caaaacagtt acccttttaaa agagatcact gtattgtcaa acatattgta ttgttcactt    3420
ttagaattac tcaaataatg cattgtaaag aattattcaa atagtgtact gcaaatagac    3480
atttcatttg aatatattta aatgatgtaa gtcatctgag gtctaataaa atcacctttt    3540
agaatttcat ctgcagaatc ttttaaagac atcttaacta cgaaaaagag attgctgatc    3600
taaattgatg atatactgtt aatacaaagc ttttggtgta tcttacatga cataacatta    3660
tgaaaaatac aatagagtat gtcatataga tgttactcta aactttaaaa aaagactaca    3720
aagtgttcta tgcataatta cattatttaa ggggaaaaag gtgttggctg acactattcc    3780
agctagacag tactgaattg caaattcatc atttgggcac agatattaat acagcttcct    3840
ctttattcct atagcattca tttgaaatcc ctgtactcca tgtcatttgc tacatatgaa    3900
acaaattgtc aagtttttaa ccacttgtgt agtttaataa aagagattaa aatcattgtc    3960
ttggaaacat caggtgtttt tcaaaattct attttattat ctttcatcaa aattttatct    4020
caaga                                                                4025
```

<210> SEQ ID NO 26
<211> LENGTH: 6149
<212> TYPE: DNA
<213> ORGANISM: Artificial Sequence
<220> FEATURE:
<223> OTHER INFORMATION: A synthetic oligonucleotide

```
<400> SEQUENCE: 26
tctagagtcg agcagtgtgg ttttcaagag gaagcaaaaa gcctctccac ccaggcctgg      60
aatgtttcca cccaatgtcg agcagtgtgg ttttgcaaga ggaagcaaaa agcctctcca     120
cccaggcctg gaatgtttcc acccaatgtc gagcaaaccc cgcccagcgt cttgtcattg     180
gcgaattcga acacgcagat gcagtcgggg cggcgcggtc ccaggtccac ttcgcatatt     240
aaggtgacgc gtgtggcctc gaacaccgag cgaccctgca gcgacccgct taacagcgtc     300
aacagcgtgc cgcagatctt ggtggcgtga aactcccgca cctcttcggc cagcgccttg     360
tagaagcgct tatggcttcg taccccggcc atcagcacgc gtctgcgttc gaccaggctg     420
cgcgttctcg cggccatagc aaccgacgta cggcgttgcg ccctcgccgg cagcaagaag     480
ccacggaagt ccgcccggag cagaaaatgc ccacgctact gcgggtttat atagacggtc     540
cccacgggat ggggaaaacc accaccacgc aactgctggt ggccctgggt tcgcgcgacg     600
atatcgtcta cgtacccgag ccgatgactt actggcgggt gctgggggct tccgagacaa     660
tcgcgaacat ctacaccaca caacaccgcc ttgaccaggg tgagatatcg gccggggacg     720
cggcggtggt aatgacaagc gcccagataa caatgggcat gccttatgcc gtgaccgacg     780
ccgttctggc tcctcatatc ggggggggagg ctgggagctc acatgccccg ccccggccc     840 tcaccctcat cttcgaccgc catcccatcg ccgccctcct gtgctacccg gccgcgcgat     900
accttatggg cagcatgacc cccaggccg tgctggcgtt cgtggccctc atcccgccga     960
ccttgcccgg cacaaacatc gtgttggggg cccttccgga ggacagacac atcgaccgcc    1020
tggccaaacg ccagcgcccc ggcgagcggc ttgacctggc tatgctggcc gcgattcgcc    1080
gcgtttacgg gctgcttgcc aatacggtgc ggtatctgca gggcggcggg tcgtggcggg    1140
aggattgggg acagctttcg gggacggccg tgccgcccca gggtgccgag ccccagagca    1200
acgcgggccc acgaccccat atcggggaca cgttatttac cctgtttcgg gcccccgagt    1260
tgctggcccc caacggcgac ctgtacaacg tgtttgcctg ggccttggac gtcttggcca    1320
aacgcctccg tcccatgcac gtctttatcc tggattacga ccaatcgccc gccggctgcc    1380
gggacgccct gctgcaactt acctccggga tgatccagac ccacgtcacc accccaggct    1440
ccataccgac gatctgcgac ctggcgcgca cgtttgcccg ggagatgggg gaggctaact    1500
gaaacacgga aggagacaat accggaagga acccgcgcta tgacggcaat aaaaagacag    1560
aacagacatg ataagataca ttgatgagtt tggacaaacc acaactagaa tgcagtgaaa    1620
aaaatgcttt atttgtgaaa tttgtgatgc tattgcttta tttgtgaaat ttgtgatgct    1680
attgctttat ttgtaaccat tataagctgc aataaacaag ttaacaacaa caattgcatt    1740
cattttatgt ttcaggttca gggggaggtg tgggaggttt tttaaagcaa gtaaacctc     1800 tacaaatgtg gtagatccat ttaaatgtta attaaagcag gaaaacatgt cccatgagac    1860
ctatacacac acacattctg ccttcagaat tcagctgctg cattctgctg ctgcttctct    1920
tattcagact gttggcatca tcaatacata acttttgatt gaatcccaag ggggaaaaat    1980
aactttggta gacagtggat acataacaaa tgcatggatt attctgggca ttccttttta    2040
tttggtagag tgaaattttt ggtgttgttg agaggataaa aaaggcattt aaaagtcaat    2100
tttgaatccg gattttctgc tctgttaata aattcacatg aaagttacag aaagtattgt    2160
tatgcttttg tactgaatag tttttgtgtt tagaaggctt taaaagcaag tactatgtcc    2220
actgtgctat tctggtttgg atattaatca gaacacagtt gagcattgtt tgaattcaca    2280
```

```
gagcttgcca tgctggaagc acaaccttat atgtagtgac catggacagt cctattatgg   2340
gaaaccaact tgagagagaa ggcgggtcac ttgcttgtgc gcaggtcctg gaatttgaaa   2400
tatccggggg cctctacaga atcctggcat cagttactgt gttgactcac tcagtgttgg   2460
gatcactcac tttcccccta caggactcag atctgggagg caattacctt cggagaaaaa   2520
cgaataggaa aaactgaagt gttacttttt ttaaagctgc tgaagtttgt tggtttctca   2580 ttgttttaa gcctactgga gcaataaagt ttgaagaact tttaccaggt ttttttatc   2640 gctgccttga tatacacttt tcaaagtaag tatcaaggtt acaagacagg tttaaggaga   2700
ccaatagaaa ctgggcttgt cgagacagag aagactcttg cgtttctgat aggcacctat   2760
tggtcttact gacatccact ttgcctttct ctccacagct cgagtcgcgg ccgcagaca   2820 tgataagata cattgatgag tttgacaaa ccacaactag aatgcagtga aaaaaatgct   2880
ttatttgtga aatttgtgat gctattgctt tatttgtgaa atttgtgatg ctattgcttt   2940
atttgtaacc attataagct gcaataaaca agttaacaac aacaattgca ttcattttat   3000
gtttcaggtt caggggggagg tgtgggaggt tttttaaagc aagtaaaacc tctacaaatg   3060
tggtagatcc atttaaatgt taattaaata acttcgtata gcatacatta tacgaagtta   3120
tggatctgcg atcgctccgg tgcccgtcag tgggcagagc gcacatcgcc cacagtcccc   3180
gagaagttgg gggagggggt cggcaattga accggtgcct agagaaggtg gcgcggggta   3240
aactgggaaa gtgatgtcgt gtactggctc cgccttttc ccgagggtgg gggagaaccg   3300
tatataagtg cagtagtcgc cgtgaacgtt ctttttcgca acgggtttgc cgccagaaca   3360
cagctggtgg gtagggatga gggagggagg ggcattgtga tgtacagggc tgctctgtga   3420
gatcaagggt ctcttaaggg tgggagctgg ggcagggact acgagagcag ccagatgggc   3480
tgaaagtgga actcaagggg tttctggcac ctacctacct gcttcccgct gggggtgg   3540 gagttggccc agagtcttaa gattggggca gggtggagag gtgggctctt cctgcttccc   3600
actcatctta tagctttctt tccccagatc cgaattcgag atccaaacca aggaggaaag   3660
gatatcacag aggagaatgg tgagcaaggg cgaggagctg ttcaccgggg tggtgcccat   3720
cctggtcgag ctggacggcg acgtaaacgg ccacaagttc agcgtgtctg gcgagggcga   3780
gggcgatgcc acctacggca agctgaccct gaagttcatc tgcaccaccg gcaagctgcc   3840
cgtgccctgg cccaccctcg tgaccaccct gacctacggc gtgcagtgct tcagccgcta   3900
ccccgaccac atgaagcagc acgacttctt caagtccgcc atgcccgaag gctacgtcca   3960
ggagcgcacc atcttcttca aggacgacgg caactacaag acccgcgccg aggtgaagtt   4020
cgagggcgac accctggtga accgcatcga gctgaagggc atcgacttca aggaggacgg   4080
caacatcctg ggcacaaagc tggagtacaa ctacaacagc cacaacgtct atatcatggc   4140
cgacaagcag aagaacggca tcaaggcgaa cttcaagatc cgccacaaca tcgaggacgg   4200
cagcgtgcag ctcgccgacc actaccagca gaacaccccc atcggcgacg gccccgtgct   4260
gctgcccgac aaccactacc tgagcaccca gtccgccctg agcaaagacc ccaacgagaa   4320
gcgcgatcac atggtcctgc tggagttcgt gaccgccgcc gggatcactc tcggcatgga   4380
cgagctgtac aagtaaagag ccgagggcag gggaagtctt ctaacatgcg gggacgtgga   4440
ggaaaatccc gggcccatcg aacaagacgg cctccatgct ggcagtcccg cagcttgggt   4500
cgaacgcttg ttcgggtacg actgggccca gcagaccatc ggatgtagcg atgcggccgt   4560
gttccgtcta agcgctcaag gccggccgt gctgttcgtg aagaccgacc tgagcggcgc   4620
cctgaacgag cttcaagacg aggctgcccg cctgagctgg ctggccacca ccggcgtacc   4680
```

```
ctgcgccgct gtgttggatg ttgtgaccga agccggccgg gactggctgc tgctgggcga    4740
ggtccctggc caggatctgc tgagcagcca ccttgccccc gctgagaagg tttctatcat    4800
ggccgatgca atgcggcgcc tgcacaccct ggaccccgct acctgcccct tcgaccacca    4860
ggctaagcat cggatcgagc gtgctcggac ccgcatggag gccggcctgg tggaccagga    4920
cgacctggac gaggagcatc agggcctggc ccccgctgaa ctgttcgccc gactgaaagc    4980
ccgcatgccg gacggtgagg acctggttgt cacacacgga gatgcctgcc tccctaacat    5040
catggtcgag aatggccgct tctccggctt catcgactgc ggtcgcctag gagttgccga    5100
ccgctaccag gacatcgccc tggccacccg cgacatcgct gaggagcttg gcggcgagtg    5160
ggccgaccgc ttcttagtct tgtacggcat cgcagctccc gacagccagc gcatcgcctt    5220
ctaccgcttg ctcgacgagt tcttttaatg atctagaacc ggtcatggcc gcaataaaat    5280
atctttattt tcattacatc tgtgtgttgg ttttttgtgt gagtagtttg caaagaagca    5340
taaatgttat atatactgca tatatatatg tatttattca ggaatatata tttttcattg    5400
ggaaaacttt tcaacagaaa tggagtgtaa aagttttttct ttgcgataga actaaacaca    5460
tgatttcttg attaacaaac cactgcagta atagaatatg cagaatgtca tttgactata    5520
acagatttat tttgattgct gtgagatagt ttgtatatct gagttattat tttgattagt    5580
tgatacttcc gtatttagta acagttacat aaaggttact gacctgacat atattctcaa    5640
ttgaactaac tactgtatag gaactacatg gaggcctaaa agttagaaaa agtttctctg    5700
acacatcatg gataaaataa agaataaaat gagttgggac ggataattga aggatgtgaa    5760
aagtattgat aaagatttaa ttttaatgtt tcttactcac atttactatt tcaaatgctc    5820
ttttctgtag catatcatga taattatttc aaataatgat gtgatctatg ctatcaaatg    5880
atcagatgat ttcttgggta aacgacatac aaacttgagg aactcctaat tatatttagt    5940
agtaaagtca ccttgttgtt tcatgtctat tatgagccag cttttcagtt caatttttta    6000
gtttgtcttt catatagaaa tacaactatt tcgtttattt ttaagaaagt catgatgact    6060
aatgaaggat ttaaaaatgg actgtggcac aacagtaaaa ataatatatg ataaggactg    6120
tgtgtcccga agagatggga gtttatctc                                      6149
```